(12) United States Patent
Brown et al.

(10) Patent No.: US 10,466,212 B2
(45) Date of Patent: Nov. 5, 2019

(54) SCANNING ELECTRON MICROSCOPE AND METHODS OF INSPECTING AND REVIEWING SAMPLES

(71) Applicant: KLA-Tencor Corporation, Milpitas, CA (US)

(72) Inventors: David L. Brown, Los Gatos, CA (US); Yung-Ho Alex Chuang, Cupertino, CA (US); John Fielden, Los Altos, CA (US); Marcel Trimpl, San Jose, CA (US); Jingjing Zhang, San Jose, CA (US); Devis Contarato, San Carlos, CA (US); Venkatraman Iyer, Saratoga, CA (US)

(73) Assignee: KLA—Tencor Corporation, Milpitas, CA (US)

( * ) Notice: Subject to any disclaimer, the term of this patent is extended or adjusted under 35 U.S.C. 154(b) by 185 days.

(21) Appl. No.: 15/667,500

(22) Filed: Aug. 2, 2017

(65) Prior Publication Data
US 2017/0329025 A1 Nov. 16, 2017

Related U.S. Application Data

(62) Division of application No. 14/834,991, filed on Aug. 25, 2015, now Pat. No. 9,767,986.
(Continued)

(51) Int. Cl.
*H01J 37/244* (2006.01)
*G01N 30/72* (2006.01)
(Continued)

(52) U.S. Cl.
CPC ............... *G01N 30/72* (2013.01); *G01T 1/24* (2013.01); *G06F 19/00* (2013.01); *H01J 37/244* (2013.01);
(Continued)

(58) Field of Classification Search
CPC .. H01J 37/20; H01J 37/26; H01J 37/28; H01J 37/185; H01J 2237/24592; H01J 2237/2605; G01T 7/005; G01D 18/00
See application file for complete search history.

(56) References Cited

U.S. PATENT DOCUMENTS 3,755,704 A 8/1973 Spindt et al.
3,870,917 A 3/1975 Cuny
(Continued)

FOREIGN PATENT DOCUMENTS

CN 102670224 A 9/2012
EP 0602983 A1 6/1994
(Continued)

OTHER PUBLICATIONS

61/720700—Certified Copy corres to PCT/EP2013/071080, pp. 1-44.
(Continued)

*Primary Examiner* — David E Smith
*Assistant Examiner* — Hsien C Tsai
(74) *Attorney, Agent, or Firm* — Bever, Hoffman & Harms, LLP

(57) ABSTRACT

A scanning electron microscope incorporates a multi-pixel solid-state electron detector. The multi-pixel solid-state detector may detect back-scattered and/or secondary electrons. The multi-pixel solid-state detector may incorporate analog-to-digital converters and other circuits. The multi-pixel solid state detector may be capable of approximately determining the energy of incident electrons and/or may contain circuits for processing or analyzing the electron signals. The multi-pixel solid state detector is suitable for high-speed operation such as at a speed of about 100 MHz or higher. The scanning electron microscope may be used for reviewing, inspecting or measuring a sample such as unpat-
(Continued)

terned semiconductor wafer, a patterned semiconductor wafer, a reticle or a photomask. A method of reviewing or inspecting a sample is also described.

14 Claims, 8 Drawing Sheets

Related U.S. Application Data

(60) Provisional application No. 62/043,410, filed on Aug. 29, 2014.

(51) Int. Cl.
  *H01J 37/28* (2006.01)
  *H01L 31/00* (2006.01)
  *G01T 1/24* (2006.01)
  *G06F 19/00* (2018.01)
  *H01J 49/02* (2006.01)
  *H01L 27/146* (2006.01)

(52) U.S. Cl.
  CPC .............. *H01J 37/28* (2013.01); *H01J 49/02* (2013.01); *H01L 27/1464* (2013.01); *H01L 27/14659* (2013.01); *H01L 27/14661* (2013.01); *H01L 31/00* (2013.01); *H01J 2237/2441* (2013.01); *H01J 2237/2446* (2013.01); *H01J 2237/24475* (2013.01); *H01J 2237/24495* (2013.01); *H01J 2237/24592* (2013.01)

(56) References Cited

U.S. PATENT DOCUMENTS

| | | |
|---|---|---|
| 3,947,707 A | 3/1976 | Shannon et al. |
| 4,099,198 A | 7/1978 | Howorth et al. |
| 4,210,922 A | 7/1980 | Shannon |
| 4,275,326 A | 6/1981 | Houtkamp |
| 4,348,690 A | 9/1982 | Jastrzebski et al. |
| 4,467,189 A | 8/1984 | Tsuchiya |
| 4,555,731 A | 11/1985 | Zinchuk |
| 4,644,221 A | 2/1987 | Gutierrez et al. |
| 4,760,031 A | 7/1988 | Janesick |
| 4,853,595 A | 8/1989 | Alfano et al. |
| 5,054,683 A | 10/1991 | Haisma et al. |
| 5,120,949 A | 6/1992 | Tomasetti |
| 5,227,313 A | 7/1993 | Gluck et al. |
| 5,315,126 A | 5/1994 | Field |
| 5,376,810 A | 12/1994 | Hoenk et al. |
| 5,428,392 A | 6/1995 | Castro et al. |
| 5,563,702 A | 10/1996 | Emery et al. |
| 5,717,518 A | 2/1998 | Shafer et al. |
| 5,719,069 A | 2/1998 | Sparks |
| 5,731,584 A | 3/1998 | Beyne et al. |
| 5,742,626 A | 4/1998 | Mead et al. |
| 5,760,809 A | 6/1998 | Malhotra et al. |
| 5,760,899 A | 6/1998 | Eismann |
| 5,852,322 A | 12/1998 | Speckbacher |
| 5,940,685 A | 8/1999 | Loomis et al. |
| 5,965,910 A | 10/1999 | Wood |
| 5,999,310 A | 12/1999 | Shafer et al. |
| 6,013,399 A | 1/2000 | Nguyen |
| 6,064,759 A | 5/2000 | Buckley et al. |
| 6,162,707 A | 12/2000 | Dinh et al. |
| 6,201,601 B1 | 3/2001 | Vaez-Iravani et al. |
| 6,271,916 B1 | 8/2001 | Marxer et al. |
| 6,278,119 B1 | 8/2001 | Nikzad et al. |
| 6,285,018 B1 | 9/2001 | Aebi et al. |
| 6,297,879 B1 | 10/2001 | Yang et al. |
| 6,307,586 B1 | 10/2001 | Costello |
| 6,346,700 B1 | 2/2002 | Cunningham et al. |
| 6,362,484 B1 | 3/2002 | Beyne et al. |
| 6,373,869 B1 | 4/2002 | Jacob |
| 6,403,963 B1 | 6/2002 | Nikzad et al. |
| 6,535,531 B1 | 3/2003 | Smith et al. |
| 6,545,281 B1 | 4/2003 | McGregor et al. |
| 6,608,676 B1 | 8/2003 | Zhao et al. |
| 6,711,283 B1 | 3/2004 | Soenksen |
| 6,837,766 B2 | 1/2005 | Costello |
| 6,990,385 B1 | 1/2006 | Smith et al. |
| 7,005,637 B2 | 2/2006 | Costello et al. |
| 7,039,157 B2 | 5/2006 | Fujii et al. |
| 7,126,699 B1 | 10/2006 | Wihl et al. |
| 7,130,039 B2 | 10/2006 | Vaez-Iravani et al. |
| 7,136,159 B2 | 11/2006 | Tsai et al. |
| 7,141,791 B2 | 11/2006 | Masnaghetti et al. |
| 7,283,166 B1 | 10/2007 | Billman |
| 7,313,155 B1 | 12/2007 | Mu et al. |
| 7,321,468 B2 | 1/2008 | Herkommer et al. |
| 7,345,825 B2 | 3/2008 | Chuang et al. |
| 7,352,457 B2 | 4/2008 | Kvamme et al. |
| 7,432,517 B2 | 10/2008 | Botma et al. |
| 7,446,474 B2 | 11/2008 | Maldonado et al. |
| 7,465,935 B2 | 12/2008 | Urano et al. |
| 7,525,649 B1 | 4/2009 | Leong et al. |
| 7,528,943 B2 | 5/2009 | Brown et al. |
| 7,586,108 B2 | 9/2009 | Nihtianov et al. |
| 7,609,309 B2 | 10/2009 | Brown et al. |
| 7,714,287 B1 | 5/2010 | James et al. |
| 7,741,666 B2 | 6/2010 | Nozaki et al. |
| 7,750,280 B2 | 7/2010 | Hwang et al. |
| 7,791,170 B2 | 9/2010 | Chiang et al. |
| 7,800,040 B2 | 9/2010 | Blacksberg et al. |
| 7,813,406 B1 | 10/2010 | Nguyen et al. |
| 7,838,833 B1 | 11/2010 | Lent et al. |
| 7,875,948 B2 | 1/2011 | Hynecek et al. |
| 7,928,382 B2 | 4/2011 | Hatakeyama et al. |
| 7,952,633 B2 | 5/2011 | Brown et al. |
| 7,985,658 B2 | 7/2011 | Lei et al. |
| 7,999,342 B2 | 8/2011 | Hsu et al. |
| 8,017,427 B2 | 9/2011 | Manabe |
| 8,138,485 B2 | 3/2012 | Nihtianov et al. |
| 8,309,443 B2 | 11/2012 | Tanaka et al. |
| 8,323,406 B2 | 12/2012 | Bondokov et al. |
| 8,450,820 B2 | 5/2013 | Nanver et al. |
| 8,455,971 B2 | 6/2013 | Chen et al. |
| 8,513,587 B2 | 8/2013 | Wang et al. |
| 8,514,587 B2 | 8/2013 | Zhang et al. |
| 8,629,384 B1 | 1/2014 | Biellak et al. |
| 8,686,331 B2 | 4/2014 | Armstrong |
| 8,693,233 B2 | 4/2014 | Scheuerlein et al. |
| 8,803,075 B2 | 8/2014 | Menge et al. |
| 8,891,079 B2 | 11/2014 | Zhao et al. |
| 9,055,246 B2 | 6/2015 | Tay |
| 9,426,400 B2 | 8/2016 | Brown et al. |
| 9,478,402 B2 | 10/2016 | Chuang et al. |
| 9,496,425 B2 | 11/2016 | Chern et al. |
| 2001/0017344 A1 | 8/2001 | Aebi |
| 2002/0191834 A1 | 12/2002 | Fishbaine |
| 2003/0043876 A1 | 3/2003 | Lublin et al. |
| 2003/0222579 A1 | 12/2003 | Habib et al. |
| 2004/0021061 A1 | 2/2004 | Bijkerk |
| 2004/0056279 A1 | 3/2004 | Niigaki et al. |
| 2004/0227070 A1 | 11/2004 | Bateman et al. |
| 2005/0122021 A1 | 6/2005 | Smith et al. |
| 2005/0167575 A1 | 8/2005 | Benz et al. |
| 2005/0190452 A1 | 9/2005 | Govorkov et al. |
| 2005/0196059 A1 | 9/2005 | Inoue et al. |
| 2005/0264148 A1 | 12/2005 | Maldonado et al. |
| 2006/0054778 A1 | 3/2006 | Suhling |
| 2006/0054817 A1 | 3/2006 | Parker et al. |
| 2006/0069460 A1 | 3/2006 | Smith et al. |
| 2006/0170324 A1 | 8/2006 | Machuca et al. |
| 2006/0188869 A1 | 8/2006 | Zeskind et al. |
| 2006/0278943 A1 | 12/2006 | Turchetta et al. |
| 2007/0034987 A1 | 2/2007 | Costello et al. |
| 2007/0096648 A1 | 5/2007 | Nakajima et al. |
| 2007/0103769 A1 | 5/2007 | Kuwabara |
| 2007/0188744 A1 | 8/2007 | Leslie et al. |
| 2007/0291810 A1 | 12/2007 | Luo et al. |
| 2008/0044932 A1 | 2/2008 | Samoilov et al. |
| 2008/0173903 A1 | 7/2008 | Imai et al. |

(56) References Cited

U.S. PATENT DOCUMENTS

| | | |
|---|---|---|
| 2008/0230697 A1 | 9/2008 | Tanimoto et al. |
| 2008/0267241 A1 | 10/2008 | Brown et al. |
| 2008/0267489 A1* | 10/2008 | Xiao .................. G06T 7/001 382/147 |
| 2008/0315092 A1 | 12/2008 | Kley |
| 2009/0045325 A1 | 2/2009 | Tomuta et al. |
| 2009/0091752 A1 | 4/2009 | Terasawa et al. |
| 2009/0108207 A1 | 4/2009 | Liu |
| 2009/0125242 A1 | 5/2009 | Choi et al. |
| 2009/0128912 A1 | 5/2009 | Okada et al. |
| 2009/0168152 A1 | 7/2009 | Gelernt et al. |
| 2009/0180176 A1 | 7/2009 | Armstrong et al. |
| 2009/0324234 A1 | 12/2009 | Kashima |
| 2010/0039546 A1 | 2/2010 | Cohen et al. |
| 2010/0051804 A1 | 3/2010 | Adamec et al. |
| 2010/0102213 A1 | 4/2010 | Garris |
| 2010/0103409 A1 | 4/2010 | Ohshima et al. |
| 2010/0148667 A1 | 6/2010 | Niigaki et al. |
| 2010/0188655 A1 | 7/2010 | Brown et al. |
| 2010/0194956 A1 | 8/2010 | Yuan et al. |
| 2010/0208979 A1 | 8/2010 | Abbott et al. |
| 2010/0233869 A1 | 9/2010 | Park et al. |
| 2010/0301437 A1 | 12/2010 | Brown |
| 2010/0302424 A1 | 12/2010 | Yamaguchi |
| 2011/0073982 A1 | 3/2011 | Armstrong et al. |
| 2011/0101219 A1 | 5/2011 | Uchiyama et al. |
| 2011/0116077 A1 | 5/2011 | Chuang et al. |
| 2011/0168886 A1 | 7/2011 | Shadman et al. |
| 2011/0169116 A1 | 7/2011 | Nanver et al. |
| 2011/0234790 A1 | 9/2011 | True |
| 2011/0256655 A1 | 10/2011 | Nikzad et al. |
| 2011/0261354 A1 | 10/2011 | Sinfield et al. |
| 2011/0291109 A1 | 12/2011 | Wraback et al. |
| 2012/0012811 A1 | 1/2012 | Deflumere et al. |
| 2012/0012957 A1 | 1/2012 | Larsen et al. |
| 2012/0038809 A1 | 2/2012 | Lee et al. |
| 2012/0081684 A1 | 4/2012 | Den et al. |
| 2012/0127779 A1* | 5/2012 | Scheuerlein ............. G11C 5/02 365/148 |
| 2012/0132823 A1 | 5/2012 | Menge et al. |
| 2012/0160993 A1 | 6/2012 | Nevet et al. |
| 2012/0170021 A1 | 7/2012 | Walsh |
| 2012/0228485 A1 | 9/2012 | Iwakiri et al. |
| 2012/0268722 A1 | 10/2012 | Nihtianov et al. |
| 2013/0009069 A1 | 1/2013 | Okada |
| 2013/0015324 A1 | 1/2013 | Park et al. |
| 2013/0016346 A1 | 1/2013 | Romanovsky et al. |
| 2013/0017205 A1 | 1/2013 | Giaccia et al. |
| 2013/0020491 A1 | 1/2013 | Mazzillo |
| 2013/0056843 A1 | 3/2013 | Lee et al. |
| 2013/0077086 A1 | 3/2013 | Chuang et al. |
| 2013/0082241 A1 | 4/2013 | Kub et al. |
| 2013/0126705 A1 | 5/2013 | Maleev |
| 2013/0148112 A1 | 6/2013 | Chuang et al. |
| 2013/0169957 A1 | 7/2013 | Wolf et al. |
| 2013/0176552 A1 | 7/2013 | Brown et al. |
| 2013/0194445 A1 | 8/2013 | Brown et al. |
| 2013/0264481 A1* | 10/2013 | Chern ................. H01L 31/0216 250/358.1 |
| 2013/0270663 A1 | 10/2013 | Lin et al. |
| 2013/0313440 A1 | 11/2013 | Chuang et al. |
| 2013/0320211 A1* | 12/2013 | Park .................... H01J 37/26 250/310 |
| 2013/0336574 A1 | 12/2013 | Nasser-Ghodsi et al. |
| 2013/0341504 A1 | 12/2013 | Neill et al. |
| 2014/0034816 A1 | 2/2014 | Chuang et al. |
| 2014/0111799 A1 | 4/2014 | Lei et al. |
| 2014/0151552 A1 | 6/2014 | Jiang et al. |
| 2014/0203386 A1 | 7/2014 | Bui et al. |
| 2014/0204963 A1 | 7/2014 | Chuang et al. |
| 2014/0246595 A1 | 9/2014 | Menge et al. |
| 2014/0362203 A1 | 12/2014 | Delaney et al. |
| 2015/0177159 A1 | 6/2015 | Brown et al. |
| 2015/0200216 A1 | 7/2015 | Muramatsu et al. |
| 2015/0275393 A1 | 10/2015 | Bondokov et al. |
| 2015/0294998 A1 | 10/2015 | Nihtianov et al. |

FOREIGN PATENT DOCUMENTS

| | | |
|---|---|---|
| EP | 0746871 A1 | 12/1996 |
| EP | 1939917 A2 | 7/2008 |
| EP | 2346094 A1 | 7/2011 |
| JP | H0511287 A | 1/1993 |
| JP | H08241977 A | 9/1996 |
| JP | H10171965 A | 6/1998 |
| JP | 2003043533 A | 2/2003 |
| JP | 2004031452 A | 1/2004 |
| JP | 2007249092 A | 9/2007 |
| JP | 2007298932 A | 11/2007 |
| JP | 2009117454 A | 5/2009 |
| JP | 2010003755 A | 1/2010 |
| KR | 100688497 B1 | 3/2007 |
| KR | 100826407 B1 | 5/2008 |
| RU | 2297070 C2 | 4/2007 |
| TW | 201432252 A | 8/2014 |
| WO | 9532518 A1 | 11/1995 |
| WO | 9617372 A1 | 6/1996 |
| WO | 2007035858 A2 | 3/2007 |
| WO | 2008121232 A1 | 10/2008 |
| WO | 2011091159 A1 | 7/2011 |
| WO | 2014067754 A2 | 5/2014 |

OTHER PUBLICATIONS

Allen et al., Work Function, Photoelectric Threshold, and Surface . . . ; Physical Review, vol. 127, No. 1, Jul. 1, 1962, pp. 150-158.

Armstrong, Carter M.The Quest for the Ultimate Vacuum Tube, Spectrum IEEE, Dec. 2015, 4 pgs.

Ding, MengField Emission from Silicon, MIT 2001, 277 pgs.

Dulinski et al., Tests of a backside illuminated monolithic CMOS pixel . . . , Nuclear Instruments and Methods in Physics Research A 546 (2005) 274-280, 7 pgs.

Fanton et al, Multiparameter Measurements of Thin Film . . . , Journal of Applied Physics, vol. 73, No. 11, p. 7035 (1993).

Field Emitter Review, 7 pgs in Japanese.

Fowler, R. H., et al, Electron Emission in Intense Electric Fields, Mar. 31, 1928, 9 pgs.

Fu et al., Optimizing GaN photocathode structure for higher . . . ; Optik, vol. 123, No. 9, May 2012, pp. 756-768.

Grubisic et al., New Silicon Reach-Through Avalanche Photodiodes with Enhanced Sensitivity in the DUV/UV Wavelength Range, MIPRO 2013, May 20-24, 2013, pp. 48-54.

Hecht, Optics, Fourth Edition, India: Pearson Education Pte, Ltd. 2004.

Hecht, Optics, Second Edition, Adelphi University, 1987, Addison-Wesley Publishing Company, Inc., 3 pages.

Henderson, Brian S., Study of Negative Electron Affinity . . . , Dept. of Physics, Rice Univ., Aug. 7, 2009, 18 pgs.

Howorth et al., Transmission silicon photoemitters . . . , Jrnl of Physics D: Applied Physics, vol. 9, No. 5, Apr. 1, 1976, pp. 785-794.

Huang et al., Back-Side Illuminated Photogate CMOS . . . , IEEE Sensors Journal, vol. 11, No. 9, Sep. 2011, 5 pgs.

ISR and Written Opinion dated Mar. 31, 2014 for PCT/US2013/074124.

Itzler et al., InP-based Geiger-mode . . . , Proc. SPIE vol. 7320 (2000), 12 pgs.

Janesick, James R., Scientific Charge-Coupled Devices, SPIE Press, 2001, pp. 556-561.

Koike, AkifumiField Emitter Equipped With a Suppressor to Control Emission Angel, IEEE Electron Device Letters, vol. 34, No. 5, May 2013, 3 pgs.

Martinelli, Ramon U., Infrared Photoemission from Silicon, Applied Physics Letters, vol. 16, No. 7, Apr. 1, 1970, pp. 261-262.

Martinelli, Ramon U., Reflection and Transmission Secondary Emission . . . , Applied Physics Letters, vol. 17, No. 8, Oct. 15, 1970, pp. 313-314.

(56) References Cited

OTHER PUBLICATIONS

Nagao, Masayoshi, Cathode Technologies for Field Emission Displays, IEEJ Trans 2006; 1:171-178, 8 pgs.

Nagao, MasayoshiFabrication of a Field Emitter Array with a Built-In Einzel Lens, JJAP 48 (2008) 06FK02, 4 pgs.

Nanver et al., Pure-Boron Chemical-Vapor-Deposited Layers: a New Material for Silicon Device Processing, 18th IEEE International Conference on Advanced Thermal Processing of Semiconductors (RTP), Sep. 28, 2010-Oct. 1, 2010, pp. 136-139.

Nanver, Silicon Photodiodes for Low Penetration Depth Beams such as DUV/VUV/EUV Light and Low-Energy Electrons, Advances in Photodiodes, G. Betta, ed., Mar. 22, 2011, pp. 205-224, www.intechopen.com.

Neo, YoichiroElectron Optical Properties of Microcolumn with Field Emitter, JJAP 52 (2013) 036603, 5 pgs.

Niclass et al., Design and Characterization of a CMOS 3-D . . . , IEEE Journal Solid-State Circuits, vol. 40, No. 9, Sep. 2005, 8 pgs.

Nikzad, Shouleh et al., Delta-doped CCDs High QE with long-term stability . . . ; SPIE vol. 2198 (1994) pp. 907-915.

Omatsu et al., High repetition rate Q-switching performance . . . , Optics Express vol. 14, Issue 7, pp. 2727-2734, Apr. 3, 2006.

Paetzel et al., Activation of Silicon Wafer by Excimer Laser, 18th IEEE Conf. Advanced Thermal Processing of Semiconductors-RTP 2010, 5 pgs.

Pain; et al., "Pain et al., "A Back-Illuminated Megapixel CMOS Image Sensor", Jun. 9, 2005, IEEE Workshop on Charge-Coupled Devices and Advanced Image Sensors, Karuizawa, Japan, 4 pgs."

Rakhshandehroo, M.R. et al, Fabrication of a self-aligned silicon field emission . . . , JVSTB, 16, 765 (1998); doi: 10.1116/1,589900, 6 pgs.

Rakhshandehroo, M.R. et al, Field emission from gated Si emitter tips with precise . . . , JVSTB, 15, 2777 (1997); doi: 10.1116/1.589726, 6 pgs.

Sakic, Agata, Boron-layer silicon photodiodes for high-efficiency low-energy electron detection, Solid-State Electronics 65-66 (2011), pp. 38-44.

Sarubbi et al., Chemical Vapor Deposition of α-Boron Layers on Silicon for Controlled Nanometer-Deep p+ n Junction Formation, J. Electron. Mat., vol. 39, No. 2, Feb. 2010, pp. 162-173.

Sarubbi et al., Pure boron-doped photodiodes . . . IEEE, Sep. 15, 2008, pp. 278-281.

Sato, T., et al, Fabrication and characterization of HfC coated . . . , J. Vac. Sci. Technol. B 2194), published Jul. 31, 2003, 5 pgs.

Serbun Pavel et al, Stable field emission of single B-doped . . . , JVSTB, 31, 02B101 (2013); doi: 10.1116/1.4765088, 7 pgs.

Sobieski, Stanley, Intensified Charge Coupled Devices for Ultra Low Light Level Imaging, NASA, Goddard Space Flight Center, SPIE vol. 78 (1976) Low Light Level Devices, pp. 73-77.

Stevanovic et al., A CMOS Image Sensor for High-Speed Imaging, 2000 IEEE int'l. Solid-State Circuits Conf., 3 pgs.

Tobin, Kenneth W., Inspection in Semiconductor Manufacturing, Webster's Encyclopedia of Electrical and Electronic Engineering, vol. 10, pp. 242-262, Wiley & Sons, NY, NY, 1999.

Utsumi, TakaoVacuum Microelectrnoics: What's New and Exciting, IEEE vol. 38, No. 10, Oct. 1991, 8 pgs.

Xiaogian, Fu, Higher Quantum Efficiency by Optimizing . . . 978-1-4244-6644-3/10 IEEE, pp. 234-235.

\* cited by examiner

SCANNING ELECTRON MICROSCOPE AND METHODS OF INSPECTING AND REVIEWING SAMPLES

RELATED APPLICATIONS

The present application is a divisional of U.S. patent application Ser. No. 14/834,991, filed on Aug. 25, 2015, which claims priority to U.S. Provisional Patent Application Ser. No. 62/043,410, entitled "Scanning Electron Microscope And Methods Of Inspecting And Reviewing Samples", filed on Aug. 29, 2014, and incorporated by reference herein.

BACKGROUND OF THE DISCLOSURE

Field of the Disclosure

The present application relates to scanning electron microscopes, electron and X-ray detectors suitable for use in scanning electron microscopes, and systems and methods for reviewing and inspecting samples. The electron microscopes, detectors, systems and methods are particularly suitable for use in review and inspection systems including those used to review and/or inspect photomasks, reticles, and semiconductor wafers.

Related Art

The integrated circuit industry requires inspection tools with increasingly higher sensitivity to detect ever smaller defects and particles whose sizes may be a few tens of nanometers (nm), or less. These inspection tools must operate at high speed in order to inspect a large fraction, or even 100%, of the area of photomask, reticle or wafer, in a short period of time, e.g. one hour or less for inspection during production, or, at most, few hours for R&D or troubleshooting. In order to inspect so quickly, inspection tools use pixel or spot sizes larger than the dimensions of the defect or particle of interest, and detect just a small change in signal caused by a defect or particle. High speed inspection is most commonly performed in production using inspection tools operating with UV light. Inspection in R&D may be performed with UV light or with electrons.

Once a defect or particle has been found by high speed inspection, it is often necessary to make a higher resolution image and/or to perform material analysis to determine the origin or type of the particle or defect. This process is commonly called review. Review is usually performed with a scanning electron microscope (SEM). Review SEMs used in the semiconductor manufacturing process are typically required to review many thousands of potential defects or particles per day and so may have, at most, a few seconds per target for review. Review SEMs for the semiconductor and related industries are manufactured by KLA-Tencor Corporation (for example the eDR-7110), by Applied Materials, Inc. (for example the SEMVision G6) and other companies.

A review SEM most commonly detects secondary electrons emitted from the sample in order to form an image. An exemplary secondary electron detector for a review SEM is described in U.S. Pat. No. 7,141,791 to Masnaghetti et al. entitled "Apparatus and method for e-beam dark-field imaging". This exemplary secondary electron detector includes electron optics for collecting secondary electrons and directing them to a scintillator. The electrons are accelerated towards the scintillator so that each electron striking the scintillator causes multiple photons to be emitted. Some of those photons are captured by a light pipe and directed to one or more photomultiplier tubes. A disadvantage of this approach is that the detector is relatively slow. The light emission from scintillator has a decay time constant of several, or many, tens of ns. Furthermore scintillators have multiple time constants. The initial response may have a time constant of a few tens of ns, but light emission will continue at a low level with a much longer time constant. Photomultiplier tubes also have responses with multiple time constants. The photocathode that emits photoelectrons has one, or more, time constants. The electrons take a significant time to travel from one dynode to another and finally to the anode, which creates an additional time constant. The electron travel time can be reduced by reducing the number of dynodes, but this reduces the gain of the photomultiplier tube and so is not a desirable trade-off as it reduces the sensitivity of the SEM in order to improve the speed.

SEMs designed for review may include electron microprobe (X-ray) analysis for material identification. In order for an SEM to have image resolution of a few nm or better to provide high-quality images of nm-sized defects and particles, the sample being inspected is placed close to the final objective lens so that it is immersed in the magnetic field of that lens, thus minimizing imaging aberrations. Placing the sample close to the objective lens prevents large detectors being placed close to the sample. In particular, X-ray detectors used for microprobe or similar analysis can only collect X-rays in a small solid angle, making such systems very slow. Many tens of seconds or minutes of data acquisition time may be required per target to capture enough X-rays to determine the material composition of the target.

The final objective lens of a review SEM also limits where secondary and backscattered electron detectors may be placed and the collection voltages that can be applied to those detectors. A small potential difference (such as less than about 2 kV) between an electron detector and the sample reduces the efficiency and sensitivity of an electron detector to collect and detect low-energy electrons from the sample.

Therefore, a need arises for a high-speed high-resolution review SEM overcoming some, or all, of the above disadvantages. In particular a need arises for a high-speed high-resolution automated SEM with capability to quickly identify at least some commonly used materials. It is further desirable that capability to quickly identify materials and/or provide improved image contrast be included in a high-speed inspection SEM.

SUMMARY OF THE DISCLOSURE

The present invention is directed to a SEM that utilizes one or more solid-state electron detectors to achieve high-speed detection of either back-scattered or secondary electrons emitted from a sample by way of converting incident electrons into measurable charges entirely within a single integral semiconductor structure. Specifically, each solid-state electron detector includes a sensor that utilizes a p-type electron-sensitive layer to generate multiple electrons in response to each incident (detected) electron, utilizes an n-type buried channel layer to transfer at least some of the generated electrons to an n+ floating diffusion, and utilizes an amplifier controlled by a charge (voltage) collected on the floating diffusion to generate an output signal, wherein the p-type electron-sensitive layer, the n-type buried channel layer, the n+ floating diffusion and the amplifier comprise respective doped regions of the single integral semiconductor (e.g., epitaxial silicon) structure. Converting incident electrons into measurable charges entirely within an integral semiconductor structure in this manner is substantially faster than the conventional photon-based scintillator approach, whereby the present invention provides an SEM that is capable of substantially higher processing speeds (e.g., 100 MHz or higher) than is possible using conventional scintillator-based SEMs. The solid-state electron detectors are also smaller in size and generate smaller detector-to-sample potential differences, which facilitates producing SEMs including a back-scattered electron detector disposed close to the electron source (e.g., between the final (immersion) objective lens and the sample, or above the final objective lens) that operates at the same high operating speed as a secondary electron detector, whereby both secondary electron signals and back-scattered electron signals may be used in combination to provide higher resolution information about the sample's surface topography than can be obtained from either signal on its own. Moreover, by fabricating each electron sensor on a single semiconductor structure using known semiconductor processing techniques, the solid-state electron detectors can be lower in overall cost and require lower operating voltages than conventional scintillator-based sensors, thereby facilitating the production of SEMs that, in comparison to conventional scintillator-based SEM systems, are less expensive to produce, and exhibit substantially higher efficiency and are thus less expensive to operate.

Exemplary inspection and review SEMs utilizing one or more solid-state electron detectors of the type mentioned above are described. The SEM includes an electron source, an electron optical system (electron optics), at least one solid-state electron detector, and a computer. The electron source generates a primary electron beam that is directed towards a sample. The electron optics includes lenses and deflectors configured to de-magnify, focus and scan the primary electron beam across an area of the sample to be inspected. When the primary electron beam strikes the sample, the sample absorbs many of the electrons from the primary electron beam, but scatters some of the electrons (back-scattered electrons). The absorbed energy causes secondary electrons to be emitted from the sample, along with some X-rays and Auger electrons. A back-scattered electron (first) electron detector is positioned close to the sample, whereby analog output signals having voltage levels that are proportional to the numbers and energies of detected back-scattered electrons are converted to corresponding digital values and transmitted to the computer as corresponding (first) image data signals. The secondary electrons are detected by an optional (second) solid-state electron detector whose sensor generates analog output signals that are proportional to the numbers and energies of detected secondary electrons, which are converted to corresponding digital values and transmitted to the computer as corresponding (second) image data signals. The computer receives the first and second image data signals from the first and second solid state detectors, and then processes the received image data signals to construct an image of the area of the sample over which the primary electron beam was scanned.

In a preferred embodiment, both the secondary electron detector and the back-scattered electron detector comprise solid-state detectors. In a preferred embodiment, the back-scattered electron detector has a pure boron coating on the surface that detects electrons (i.e., the front-facing surface that faces the sample or other electron source). In another embodiment, both the back-scattered electron detector and the secondary electron detector include the pure boron coatings.

An exemplary method of inspecting or reviewing a sample is described. The method includes generating a master clock signal, generating a deflection scan synchronized with the master clock, the deflection scan causing a primary electron beam to scan an area of a sample, and generating a first pixel clock synchronized to the master clock to collect and digitize back-scattered electron signals. The method further includes determining approximately the energy of each back-scattered electron from the charge generated in each pixel. The numbers and energies of the collected back-scattered electrons may be used to determine the presence or absence of a defect or defect type, to classify a defect type, or determine a material type or material class at a location in the scanned area of the sample.

In preferred embodiments of the method, the first pixel clock, or a second pixel clock synchronized to the master clock, is used to collect and digitize secondary electrons. The secondary electrons may be used to form an image of the scanned area of the sample. The image may be formed from the combined back-scattered electron and secondary electron signals. The secondary electron signals may be used in combination with the back-scattered electron signals to determine the presence or absence of a defect or defect type, to classify a defect type, or determine a material type or material class at a location in the scanned area of the sample. The combined signals may also provide more information about the surface topography of the sample than can be obtained from either signal on its own.

According to another embodiment of the invention, an electron detector comprises an array of pixels and multiple analog-to-digital converters, where each pixel functions in the manner described above to generate an analog output signal, and each analog-to-digital converter is connected to convert the analog output signal from only one associated pixel in order to facilitate both high-speed and high-resolution detection/readout operations. The pixel array includes multiple pixels arranged in rows and columns (e.g., 16×16, 32×32, 64×64 or more), thereby facilitating the detection of incident electrons over a large area. Similar to the generalized electron sensor mentioned above, each pixel includes a p-type electron-sensitive region, an n-type buried channel layer, a floating diffusion and an amplifier circuit configured to generate an analog output signal whose level corresponds approximately to the energy of an incident electron or the numbers of electrons (i.e., a back-scattered or secondary electron) entering that pixel. By utilizing multiple analog-to-digital converters, each configured to process the output signal from one pixel, the present invention provides a multi-pixel (i.e., 4×4 or greater) electron detector capable of substantially higher operating speeds (e.g., 100 MHz or higher sampling rate for each pixel) than is possible using conventional detector arrangements. Moreover, because the output signals from multiple pixels disposed in a matrix (array) are simultaneously converted for processing, the multi-pixel electron detector of the present invention facilitates both measuring the energy of more than one incident electron received during a given detection/readout operation, and also facilitates determining the path of incident electrons by way of the location of the detecting pixel in the matrix.

In one embodiment, the pixels are fabricated on a separate semiconductor structure from the analog-to-digital converters, and output signals are transmitted from each pixel to its associated analog-to-digital converters by way of a corresponding solder ball. In a preferred embodiment, the pixels are fabricated on a layer of lightly p-doped epitaxial (epi) silicon as part of a sensor circuit, and the analog-to-digital converters are fabricated on a second semiconductor (e.g., silicon) substrate along with other digital circuitry as part of a signal processing circuit (e.g., as part of an ASIC—application-specific integrated circuit). Preferably the thickness of the epi silicon used to form the pixels is between about 40 µm and 100 µm in order to keep the time taken for electrons to drift from the electron-sensitive region to the n-type buried channel layer limited to less than about 10 ns, while providing good mechanical strength. Depending on the mechanical support provided by the substrate that the silicon is attached to, silicon thinner than 40 µm, such as between about 10 µm and 40 µm may be acceptable. In one embodiment, a pure boron coating is disposed on the electron-sensitive surface of the epi silicon. In one embodiment, in addition to the array of analog-to-digital converters the signal processing circuit includes processing circuitry configured, for example, to calculate the approximate energy of an incident electron based on the digitized output signal (image data) received from an associated pixel of the sensor circuit. In another embodiment, the signal processing circuit also includes high speed data transmission circuitry for transmitting an image data signal to an external processing system (e.g., a computer). After the sensor circuit and the signal processing circuit are fabricated, they are connected in a stacked arrangement with solder balls connected between each pixel and an associated analog-to-digital converter. Specifically, the output signal transmitted from each pixel is connected to a first pad disposed on a surface of the sensor circuit, and from the first pad by way of an associated solder ball/bump to a second pad disposed on the signal processing circuit, from which the output signal is transmitted to the input terminal of an associated analog-to-digital converter. This connection can also provide mechanical support for the sensor circuit. The various control and power signals utilized by the pixels may be transmitted by shared metal interconnects (signal lines) from a control circuit, which in turn may be connected to the signal processing circuit or another substrate by solder bumps or wire bonds.

In a preferred embodiment, the floating diffusion of each said pixel is located in the pixel's central region, and the lateral dimensions of each pixel are limited in order to facilitate sufficient time for the electrons to transfer from the buried channel layer to the floating diffusion at the high speed data collection. By locating the floating diffusion in the center of each pixel, the path any electron is required to travel through the buried channel layer to the floating diffusion is equal to one-half of the maximum lateral (e.g., diagonal) dimension of a pixel. Limiting the nominal lateral dimensions of each pixel to about 250 µm or less facilitates operating speeds of up to 100 MHz.

In one embodiment, a separate (third) substrate is electrically and/or mechanically connected to one or more of the sensor circuit and the signal processing circuit. The separate substrate may comprise silicon or a ceramic material, and may include an integrated circuit comprising circuits for processing the analog or digital signals from each pixel, and for providing high speed data transfer of the image data to an external computer or other system. Processing functions performed by the integrated circuit may include thresholding, summing, binning and/or counting data from the individual pixels. The integrated circuit preferably includes a high-speed (such as about 10 Giga-bits per second) serial transmitter for transmitting digitized data to a computer. The integrated circuit may include a serial receiver for receiving commands from the computer. The serial receiver may operate at a lower speed than the serial transmitter.

The present invention is further directed to a novel electron sensor pixel in which a resistive gate and one or more optional additional gates are utilized to drive electrons toward the centrally located floating diffusion. The resistive gate is implemented by an amorphous or polycrystalline silicon structure disposed over most of the pixel surface. A potential difference applied between an outer periphery and an inner periphery of the resistive gate creates an electric field that drives electrons in the buried channel towards a floating diffusion that is, preferably, located near the center of the pixel to speed up charge transfer. Various additional gates are fabricated on the front surface of the pixel between the resistive gate and the floating diffusion to direct and control the transfer of the charge from the buried channel to the floating diffusion and to allow reset of the floating diffusion. The pixel's amplifier is fabricated in a p-well region on the front surface of the pixel to buffer the signal collected in the floating diffusion.

DETAILED DESCRIPTION OF THE DRAWINGS

The present invention relates to an improvement in sensors for semiconductor inspection and review systems. The following description is presented to enable one of ordinary skill in the art to make and use the invention as provided in the context of a particular application and its requirements. As used herein, directional terms such as "top", "bottom", "over", "under", "upper", "upward", "lower", "down" and "downward" are intended to provide relative positions for purposes of description, and are not intended to designate an absolute frame of reference. In addition, the phrase "integral semiconductor structure" is used herein to describe a contiguous semiconductor material (e.g., silicon) substrate entirely formed during a single fabrication process (e.g., Czochralski crystal growth, sputter deposition, plasma vapor deposition, or chemical vapor deposition), as distinguished from two separate semiconductor structures (e.g., two "chips" from the same silicon wafer) that have been connected by way of adhesive, solder, or other interconnect. Various modifications to the preferred embodiment will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed.

Figure 1:
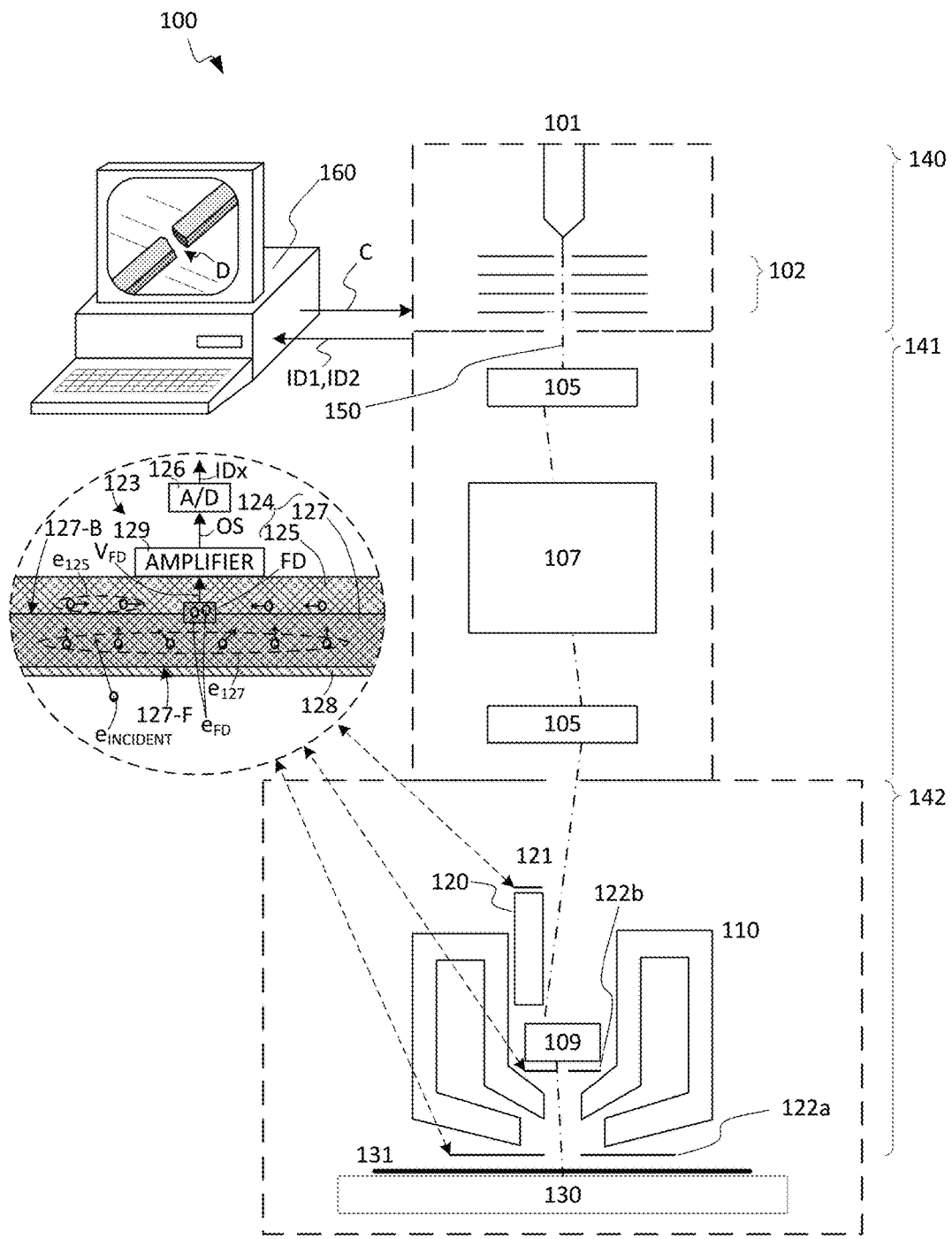
FIG. 1 illustrates an exemplary SEM incorporating a back-scattered electron detector and a secondary electron detector in accordance with an embodiment of the present invention.

FIG. 1 illustrates an exemplary scanning electron microscope (SEM) 100, also referred to as an inspection or review system configured to inspect or review a sample 131 such as a semiconductor wafer, reticle, or photomask. SEM 100 generally comprises an electron gun (source) 140, electron optics including an upper column 141 and a lower column 142, a stage 130 for supporting and positioning a sample 131, and a system computer 160.

In one embodiment electron gun 140 comprises a cathode 101 such as a thermal field-emitting or Schottky cathode, a single-crystal tungsten cathode or a $LaB_6$ cathode, and extraction and focusing electrodes 102. Electron gun 140 may further comprise a magnetic lens (not shown). Electron gun 140 generates a primary electron beam 150 with a desired beam energy and beam current.

Upper column 141 of the electron optics includes one or more condenser lenses 107 that de-magnify the primary beam to create a small spot on the sample 131. Generally spot sizes of about one or a few nm are preferred for generating high-resolution images for review of samples. Inspection of a sample may use larger spot sizes in order to scan the sample 131 more quickly. A single condenser lens 107 may suffice when the spot size is of order 100 nm or larger, but two or more condenser lenses are typically needed for spot sizes of tens of nm or smaller. Condenser lens 107 may comprise a magnetic lens, an electrostatic lens or both. Upper column 141 may also include one or more deflectors 105 that scan the primary electron beam across an area of sample 131. Deflectors 105 may be placed on either side of condenser lens 107 as shown, or within the condenser lens 107 (not shown), or after the condenser lens 107. Deflectors 105 may comprise electrostatic deflectors or a combination of magnetic and electrostatic deflectors. In one embodiment, there may be no deflectors in the upper column 141. Instead all the deflectors may be contained in lower column 142.

Lower column 142 includes a final (immersion) lens 110 for focusing the primary electron beam to a small spot on the sample 131. Final lens 110 may comprise a magnetic lens (as shown) or a combination of a magnetic lens and an electrostatic lens (not shown). In order to achieve a small spot size at the sample 131, final lens 110 is placed close to the sample 131, so that the sample is immersed in the magnetic field of the lens. This can reduce aberrations in the electron spot on the sample 131. Lower column 142 also includes deflectors 109 that work in combination with deflectors 105 (if present) to scan the primary electron beam across an area of the sample 131.

Sample 131 is placed on a stage 130 in order to facilitate movement of different regions of sample 131 underneath the electron column. Stage 130 may comprise an X-Y stage or an R-θ stage, and in one embodiment is configured to support and position numerous sample types typically reviewed by the integrated circuit industry (e.g., an unpatterned semiconductor wafer, a patterned semiconductor wafer, a reticle or a photomask). In preferred embodiments, stage 130 can adjust the height of sample 131 during inspection to maintain focus. In other embodiments, final lens 110 can be adjusted to maintain focus. In some embodiments, a focus or height sensor (not shown) may be mounted on or proximate to final lens 110 in order to provide a signal to adjust the height of sample 131 or to adjust the focus of the final lens 110. In one embodiment, the focus sensor or height sensor may be an optical sensor.

Secondary electrons and back-scattered electrons are emitted from an area of the sample 131 when the primary electron beam 150 is scanned by the electron optics across the area. Secondary electrons may be collected and accelerated by electrodes 120 and directed to secondary electron detector 121. Electron optics for collecting, accelerating and/or focusing secondary electrons are described in U.S. Pat. No. 7,141,791 to Masnaghetti et al., entitled "Apparatus and method for e-beam dark-field imaging". This patent is incorporated by reference herein. As described in the '791 patent, the electron optics for the secondary electron detector may include de-scanning optics for, at least, partially canceling the effects of the deflectors 109 on the trajectories of the secondary electrons. In some embodiments of this invention the de-scanning electron optics are not needed and may be omitted, as the de-scanning may be approximately achieved by an ASIC included within the secondary electron detector as described herein. Secondary electron detector 121 is preferably a solid-state electron detector, such as one of the solid-state electron detectors described herein, and is configured to generate an image data signal ID2 in accordance with detected secondary electrons, wherein image data signal ID2 is transferred to computer 160 and utilized to generate an image of the associated scanned sample area, whereby visual inspection of a defect D is facilitated. Other electron optics and detector configurations and methods for detecting and analyzing secondary electrons that may be used in combination with the systems and methods described herein are described in U.S. Pat. No. 7,838,833, to Lent et al., entitled "Apparatus and method for e-beam dark imaging with perspective control", and U.S. Pat. No. 7,714,287 to James et al., entitled "Apparatus and method for obtaining topographical dark-field images in a scanning electron microscope". Both of these patents are incorporated by reference herein.

Back-scattered electrons may be detected by a back-scattered electron detector, such as those shown at 122a and 122b, which is implemented by one of the solid-state electron detectors described herein, and is configured to generate an image data signal ID1 in accordance with detected back-scattered electrons, where data signal ID1 is transferred to computer 160 and is also utilized to generate the image of the associated scanned sample area. Preferably the back-scattered electron detector is placed as close as possible to the sample 131, such as at location 122a (i.e., between final lens 110 and sample 131). However the gap between the sample 131 and the final lens 110 may be small, such as about 2 mm or less, and clearance may be needed, for example, for a focus or height sensor, and so it may not be practical to place the back-scattered electron detector at location 122a. Alternatively the back-scattered electron detector may be placed at location such as 122b, on the other side of the final lens 110 pole pieces from the sample 131. Note that the back-scattered electron detector must not block primary electron beam 150. The back-scattered electron detector may have a hole in the middle or may comprise multiple detectors (such as two, three or four separate detectors) disposed around the path of the primary electron beam 150 so as not to block that path, while being efficient for capturing back-scattered electrons.

The landing energy of the primary electron beam 150 on the sample 131 depends on the potential difference between the cathode 101 and the sample 131. In one embodiment, the stage 130 and sample 131 may be held close to ground potential, and the landing energy adjusted by changing the potential of the cathode 101. In another embodiment, the landing energy on the sample 131 may be adjusted by changing the potential of the stage 130 and sample 131 relative to ground. In either embodiment, the final lens 110 and the back-scattered electron detector 122a and/or 122b must all be at potentials close to one another and close to that of the sample 131 and stage 130 (such as less than about 1000V relative to the sample 131 and stage 130) in order to avoid arcing to the sample 131. Because of this small potential difference, back-scattered electrons from the sample 131 will be accelerated only a small amount, or not at all, from the sample to the back-scattered electron detector 122a and/or 122b. Since the landing energy on the sample 131 may be quite low (such as between about 500 eV and 2 keV) for some semiconductor samples in order to avoid damage to those samples, the energy of the back-scattered electrons as they land on the back-scattered electron detector 122a and/or 122b will be quite low. Thus it is important for the sensitivity of the SEM that the back-scattered electron detectors 122a and 122b generate many electron-hole pairs from a single low-energy back-scattered electron (such as an electron having an energy of about 2 keV or less). Conventional silicon detectors unavoidably have a thin oxide, such as a native oxide, coating on the surface of the silicon, which blocks most electrons with energies below about 2 keV from reaching the silicon, or alternatively have a thin metal (such as Al) coating on the surface which scatters and absorbs a significant fraction of incident low-energy electrons. In a preferred embodiment, solid-state electron detectors described herein have a pin-hole free pure boron coating on their surface. A pin-hole free pure boron coating prevents oxidation of the silicon and allows efficient detection of low energy electrons (including electrons with energies less than 1 keV). Methods for fabricating silicon detectors with pin-hole free pure boron coatings and the design of such detectors are described in U.S. Published Patent Application 2013/0264481 entitled "Back-illuminated Sensor With Boron Layer", and filed by Chern et al. on Mar. 10, 2013. This patent application is incorporated herein by reference.

The bubble located in the lower-left portion of FIG. 1 illustrates a simplified solid-state sensor 123 utilized by one or more of electron detectors 121, 122a and 122b to convert incident back-scattered or secondary electrons $e_{INCIDENT}$ into measurable charges entirely within a single integral semiconductor (e.g., epitaxial silicon) structure 124. Sensor 123 includes a p-type electron-sensitive layer 127 configured to generate multiple electrons $e_{127}$ in response to each incident electron $e_{INCIDENT}$ that enters through a front-side surface 127-F, an n-type buried channel layer 125 configured to transfer electrons $e_{125}$, which represent at least some of generated electrons $e_{125}$, to an n+ floating diffusion FD, an amplifier 129 that generates an output signal OS according to a charge (voltage) $V_{FD}$ collected on floating diffusion FD. Buried channel layer 125 is disposed on a top surface 127-B of the electron-sensitive layer 127 to facilitate efficient collection of electrons $e_{127}$ generated by electron-sensitive layer 127, and floating diffusion FD is disposed in buried channel layer 125 to facilitate receiving electrons $e_{125}$, whereby the measured charge (voltage) $V_{FD}$ is made proportional to the number of electrons $e_{FD}$ captured by floating diffusion FD. According to an aspect of the invention, p-type electron-sensitive layer 127, n-type buried channel layer 125, n+ floating diffusion FD and amplifier 129 are collectively fabricated by diffused dopants on integral semiconductor structure 124, whereby the entire incident-electron-to-readout conversion takes place entirely within semiconductor structure 124. An optional pure boron layer 128 is formed on bottom surface 127-F of electron-sensitive layer 127 such that incident electron $e_{INCIDENT}$ passes through pure boron layer 128 before entering electron-sensitive layer 127. As discussed in additional detail below, in addition to sensor 123 each solid-state electron detector includes at least one analog-to-digital converter 126 that converts output signal OS to a digital form for transmission as digital image data signal IDx (i.e., signal ID1 in the case of back-scattered electron detectors 122a or 122b, or signal ID2 in the case of secondary electron detector 121) to computer 160.

The various circuits and systems of SEM 100 are described above in a simplified form for brevity, and it is understood that these circuit and systems include additional features and perform additional functions. For example, although back-scattered electron detectors 122a/122b and secondary electron detector 121 of SEM 100 are described above as including simplified sensor 123 to introduce certain key features of the present invention with brevity, it is understood that back-scattered electron detectors 122a/122b and secondary electron detector 121 are preferably implemented using the multi-pixel electron detectors described below. Moreover, in addition to generating images of scanned sample areas, computer 160 may be configured to perform additional functions, such as determining the presence of a defect and/or the type of the defect based on incident electron energy values indicated by the image data signals using the methods described below.

Figure 2:
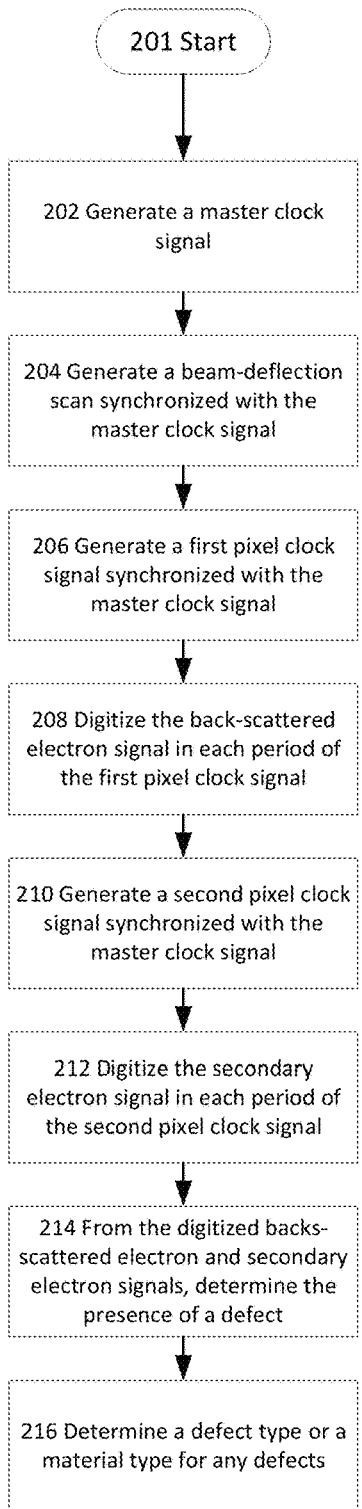
FIG. 2 illustrates an exemplary method of inspecting or reviewing a sample.

FIG. 2 illustrates an exemplary method 200 of inspecting or reviewing a sample such as a semiconductor wafer, reticle or photomask. The method illustrated in FIG. 2 may be repeated for each area on the sample that is to be inspected or reviewed. In a review SEM, the areas to be reviewed may have previously been identified by an optical or SEM inspection as potentially containing a defect or particle.

For each area on the sample to be inspected or reviewed, the exemplary method 200 starts at step 201. A master clock signal is generated at step 202 that is used to control the timing of the scanning of the primary electron beam and the acquisition of image data.

A beam-deflection scanning pattern is generated at step 204. This beam-deflection scanning pattern generates voltages and/or currents that go to beam deflectors such as those shown at 105 and 109 in FIG. 1. The pattern may be a raster scan, a serpentine pattern, a square spiral or other pattern that covers the area of the sample. A scanning pattern may also contain, for example, delays and dummy scans where no data is collected to control charge-up of the sample surface.

A first pixel clock signal is generated at step 206. The first pixel clock signal is synchronized with the master clock signal. The first pixel clock signal may be at the same frequency as the master clock signal, a frequency that is a multiple of the master clock signal, a frequency that is a sub-multiple of the master clock signal (i.e. the master clock signal frequency divided by an integer), or a frequency that is a rational multiple of the master clock signal frequency.

In step 208, on each period of the first pixel clock signal, signals collected in the back-scattered electron detector are read out and digitized.

In step 210, a second pixel clock signal is generated that is synchronized to the master clock signal. The second pixel clock signal may be at the same frequency as the master clock signal, a frequency that is a multiple of the master clock signal, a frequency that is a sub-multiple of the master clock signal (i.e. the master clock signal frequency divided by an integer), or a frequency that is a rational multiple of the master clock signal frequency. The second pixel clock signal may be at the same frequency as the first pixel clock signal. In one embodiment the first pixel clock signal is used for both the first and second pixel clock signals and no separate second pixel clock signals is generated.

In step 212, on each period of the second pixel clock signal (or the first pixel clock signal if no second pixel clock signal is used), signals collected in the secondary electron detector are read out and digitized.

In step 214, the digitized back-scattered and secondary electron signals are used to determine the presence of one or more defects in the scanned area. A defect may comprise the presence of material (such as a particle) that is not supposed to be there, the absence of material that is supposed to be there (such as may happen with an over-etched condition), or a malformed pattern.

In an optional step 216, for each defect found in step 214, the defect type or the material type of the defect may be determined. For example, high atomic number elements generally scatter a greater fraction of incident electrons than low atomic number elements. The back-scattered electron signal may be used to infer the presence or absence of a high-atomic number element (such as a metal). In step 216, when an area is being reviewed that has previously been inspected, the prior inspection data (optical and/or e-beam) may be used in combination with the digitized back-scattered and secondary electron signals in order to better determine the defect or material type. In one embodiment, steps 214 and 216 may be combined into a single step that simultaneously determines the presence and type of a defect.

Method 200 may be repeated from the beginning for each area on the sample to be reviewed or inspected.

Figure 3A:
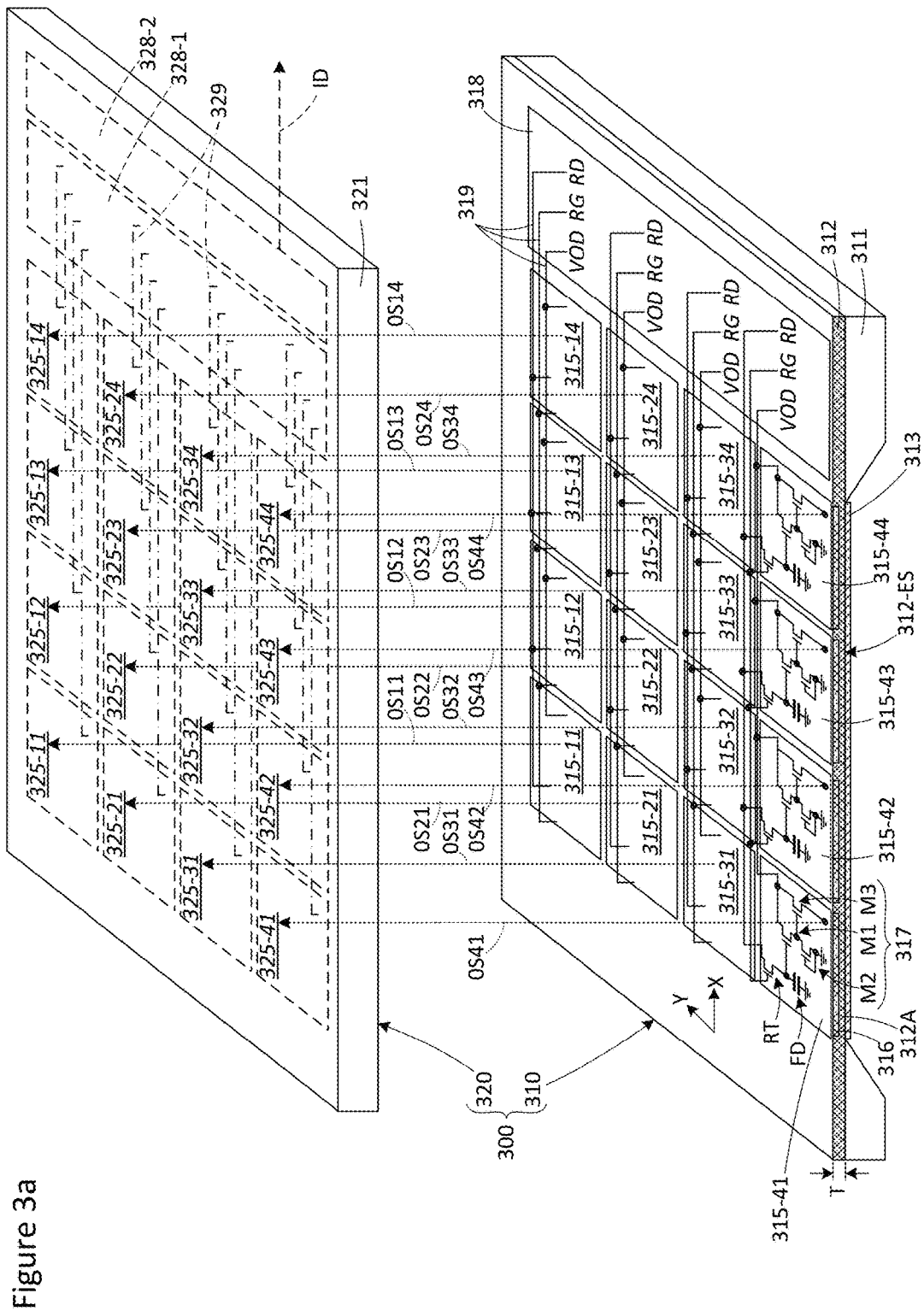
FIGS. 3a, 3b and 3c illustrate key aspects of an exemplary solid-state electron detector comprising multiple pixels with one output per pixel in accordance with an embodiment of the present invention.

FIG. 3a illustrates an exemplary simplified multi-pixel electron detector 300 for use in a review SEM or other SEM system, such as SEM 100 shown in FIG. 1. Electron detector 300 generally includes a sensor circuit 310 and a signal processing circuit 320. In the preferred embodiment illustrated in FIG. 3a, sensor circuit 310 is fabricated on a silicon structure (chip) 311, and signal processing circuit 320 is fabricated on a separate silicon structure (chip) 321 for reasons that will become clear below. In an alternative embodiment (not shown), both sensor and signal processing circuits are fabricated on the same silicon chip.

Referring to the lower portion of FIG. 3a, sensor 310 includes sixteen pixels 315-11 to 315-44 disposed in a four-row, four-column (4×4) array. For descriptive purposes, "rows" of pixels are aligned in the arbitrarily assigned X-axis direction in FIG. 3a, whereby pixels 315-11 to 315-14 form a first row, pixels 315-21 to 315-24 form a second row, pixels 315-31 to 315-34 form a third row, and pixels 315-41 to 315-44 form a fourth row. Similarly, "columns" of pixels are aligned in the Y-axis direction shown in FIG. 3a, whereby pixels 315-11 to 315-41 form a first column, pixels 315-12 to 315-42 form a second column, pixels 315-13 to 315-43 form a third column, and pixels 315-14 to 315-44 form a fourth column. In practical applications, sensor circuits are expected to include arrays of 16×16, 32×32, 64×64 or more pixels, where the pixels of these larger arrays include features similar to those of the simplified 4×4 array described below. Moreover, the numbers of pixels in each row/column of the array need not be powers of two, nor do the number of pixels in each row need to be equal to the number of pixels in each column. In one embodiment (e.g., in the case of back-scattered electron detectors 122a or 122b, shown in FIG. 1), sensor 310 includes a hole (not shown) in the middle of the sensor to allow the primary electron beam to pass through the sensor. Although pixels 315-11 to 315-44 are depicted as having square shapes, the pixels may also be rectangular or hexagonal.

According to an aspect of the invention, each pixel of sensor circuit 310 includes electron-sensitive, buried channel, floating diffusion and amplifier circuit structures similar to those described above with reference to FIG. 1. By way of example, referring to pixel 315-41 in FIG. 3a, each pixel generally includes a p-type electron-sensitive region 312A, an n-type buried channel layer 316, a floating diffusion FD, and an amplifier 317. P-type electron-sensitive region 312A is formed by the portion of epi layer 312 located below pixel 315-41, and functions in the manner described above with reference to FIG. 1 to generate multiple electrons in response to incident electrons. Buried channel layer 316 is formed by an n-type dopant diffused into epi layer 312 over electron-sensitive region 312A, and functions to transmit electrons generated by electron-sensitive region 312A to floating diffusion FD. Floating diffusion FD, which is illustrated using a schematic capacitor signal for descriptive purposes, is formed by an n+ dopant diffused into buried channel layer 316, and functions to collect at least some of the multiple electrons generated by electron-sensitive region 312A, thereby generating a corresponding charge (voltage) in the manner described above with reference to FIG. 1. Amplifier 317 includes transistors M1, M2 and M3, and functions to generate associated output signal OS41 whose voltage level is determined by a number of electrons collected on floating diffusion FD at any given readout operation. Each pixel also includes a reset transistor RT that functions to reset the voltage level of pixel floating diffusion FD after each readout operation.

Sensor circuit 310 is depicted in FIG. 3a in a cut-away fashion to illustrate a preferred embodiment in which pixels 315-11 to 315-44 are fabricated on a membrane structure including epitaxial (epi) layer 312 and a boron layer 313. In one embodiment, substrate 311 is a p+ (i.e. highly p doped) substrate, and epi layer 312 is a p– epi layer (i.e. a layer with a low concentration of p dopant). Preferably a thickness T of epi layer 312 is between about 40 µm and 100 µm in order to keep the time taken for electrons to drift from the electron-sensitive region to the buried channel layer limited to less than about 10 ns, while providing good mechanical strength. Depending on the mechanical support provided by substrate 311, epi layer 312 may be made thinner than 40 µm, such as between about 10 µm and 40 µm. After epi layer 312 is formed, one or more additional layers (not shown) are formed over epi layer 312 (e.g., a gate oxide layer, a silicon nitride gate layer, and one or more dielectric layers), and one or more doped regions are formed in epi layer 312 (e.g., n-type buried channel portions 316, n+ floating diffusion FD, channel regions associated with a reset transistor RT and an amplifier 317, along with doped regions associated with front-side circuit elements (not shown) forming control circuit 318, which is disposed in peripheral regions of the pixel array). Forming the various pixel transistors and front-side circuit elements includes implanting or doping portions of the front side of the epi layer, and may involve patterning the gate layer. The portion of substrate 311 disposed below pixels 315-11 to 315-44 is then removed (thinned) to expose electron sensitive (front-side) surface 312-ES, and then boron layer 313 is formed on electron sensitive surface 312-ES. Additional detail related to the formation of the membrane structure depicted in FIG. 3a is provided, for example, in co-owned and co-pending U.S. Published Patent application 2013-0264481 entitled "Back-illuminated Sensor With Boron Layer", and filed by Chern et al. on Mar. 10, 2013, which is incorporated herein by reference in its entirety.

Figure 3B:
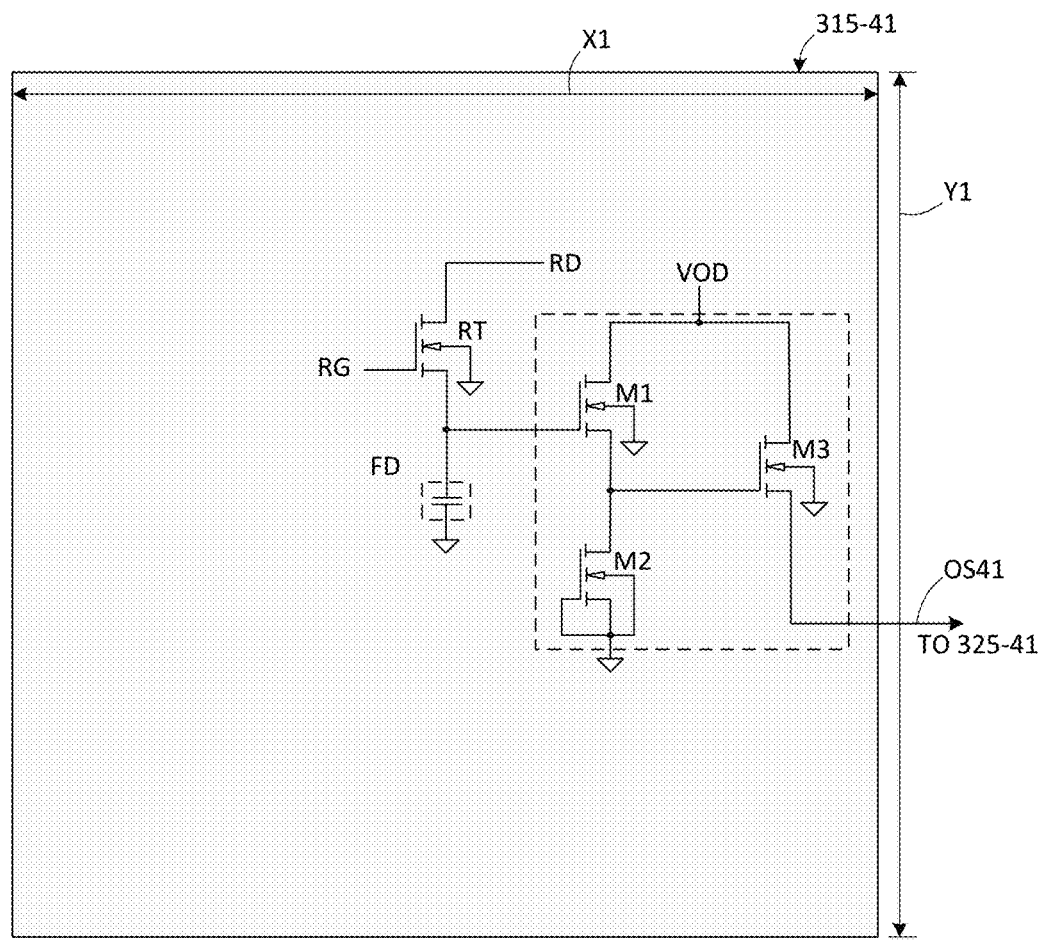

FIG. 3b is a simplified diagram showing an exemplary pixel 315-41 of FIG. 3a in additional detail. Specifically, amplifier 317 includes a first NMOS transistor M1 having a drain terminal connected to a voltage source VOD, and a gate terminal connected to and controlled by the charge stored on floating diffusion FD, and a source terminal connected to the drain terminal of a second NMOS transistor M2 and the gate terminal of a third NMOS transistor M3. The gate and source terminals of transistor M2 are connected to ground, and the drain terminal of transistor M3 is connected to voltage source VOD, whereby the output terminal of amplifier 317 is formed by the source terminal of transistor M3. Pixel 315-41 also includes an NMOS reset transistor RT having a source terminal connected to floating diffusion FD, a gate terminal controlled by a reset control signal RG, and a drain terminal connected to a reset voltage RD. During operation of pixel 315-41, each detection/readout cycle begins by resetting floating diffusion FD to voltage RD by way of toggling reset transistor RT, then waiting a predetermined detection period, then sampling output signal OS41. If zero incident (i.e., back-scattered or secondary) electrons enters the electron-sensitive region of pixel 315-41 during the detection period, the voltage levels on floating diffusion FD and output signal OS41 do not change significantly from the reset values at readout. If one or more incident (i.e., back-scattered or secondary) electrons enters the electron-sensitive region of pixel 315-41 during the detection period, the voltage level on floating diffusion FD changes (becomes more negative) by an amount proportional to the number and energy of the incident electron (which is indicated by the number of electrons accumulated in floating diffusion FD), whereby the voltage level of output signal OS41 at readout provides the approximate energy level of the incident electron detected during that detection/readout cycle (or sum of energies if multiple electrons are incident during that detection/readout cycle). When operated at a 100 MHz operating speed, 100 million detection/readout cycles are performed each second on each pixel.

According to a preferred embodiment of the present invention depicted in FIG. 3b, the floating diffusion of each pixel is located in a central region of its pixel, and the nominal lateral size dimension of each pixel is approximately 250 μm or less to facilitate the transfer of electrons to the floating diffusion during each detection/readout cycle. Referring briefly to FIG. 3a, lateral size dimensions are measured in the X-Y plane horizontal to silicon structure 311, and represent the area occupied by each pixel. Referring to FIG. 3b, floating diffusion FD is located in a central region C (FIG. 4a) of the area occupied by pixel 315-41, where the width of pixel 315-41 is indicated by width dimension X1, and the length of pixel 315-41 is indicated by dimension Y1. According to the presently preferred embodiment, both dimensions X1 and Y1 are approximately 250 μm or less to facilitate high speed readout operations. Because of the drift velocity of electrons in silicon, when readout of pixel 315-41 at a data rate of about 100 MHz or higher is desired, it is preferable that the lateral dimensions of each pixel do not exceed about 250 μm so that electrons can be driven to the centrally located floating diffusion FD in about 10 ns or less. For lower speed operation, pixels larger than 250 μm may be acceptable. For operation at speeds much higher than 100 MHz, pixel dimensions smaller than 250 μm are preferred.

Referring to the upper portion of FIG. 3a, analog-to-digital converters 325-11 to 325-44 are fabricated on semiconductor substrate 321 along with optional signal processing circuitry 328-1 and optional signal transmission circuitry 328-2 according to known techniques. In one embodiment, to facilitate the one-to-one signal connection between pixels 315-11 to 315-44 and analog-to-digital converters 325-11 to 325-44 discussed below, analog-to-digital converters 325-11 to 325-44 are arranged in a pattern that generally mirrors the array pattern (matrix) formed by pixels 315-11 to 315-44. Digital values generated by analog-to-digital converters 325-11 to 325-44 are transmitted by conductors 329 to processing circuitry 328-1 configured, for example, to calculate the approximate energy of an incident electron based on the digitized output signal (image data) received from an associated pixel of the sensor circuit. Optional high speed data transmission circuitry 328-2 is utilized, for example, to transmit image data signal ID to an external processing system (e.g., a computer).

In one embodiment, in addition to the array of analog-to-digital converters 325-xx the signal processing circuit 320 includes processing circuitry 328-1 configured, for example, to calculate the approximate energy of an incident electron based on the digitized output signal (image data) received from an associated pixel of the sensor circuit. In another embodiment, the signal processing circuit 320 also includes high speed data transmission circuitry 328-2 for transmitting an image data signal ID to an external processing system (e.g., a computer)

Referring again to the lower portion of FIG. 3a, each output signal OS11 to OS44 respectively generated by pixels 315-11 to 315-44 is transmitted by way of an associated conductive path (indicated by dotted lines) to an associated analog-to-digital converter 325-11 to 325-44 disposed on signal processing circuit 320. For example, pixel 315-11 transmits output signal OS11 by way of a dedicated conductive path to analog-to-digital converter 325-11, pixel 315-12 transmits output signal OS12 directly to analog-to-digital converter 325-12, etc. In the preferred embodiment described below with reference to FIG. 3c, output signals OS11 to OS44 may be transmitted by way of metal pads, solder balls/bumps, or similar structures that provide individual signal paths between each pixel and its associated analog-to-digital converter.

As explained herein, each pixel has multiple signals or electrical connections, such as gates, control signals, power supply and ground. The interconnect density would be too high for practical and cost-effective assembly to individually connect each of these signals to each pixel. Preferably most, or all, of these signals are connected together between neighboring pixels and brought to a convenient location, such as near the edge of the sensor where an external electrical connection can be made. For example, as indicated in FIG. 3a, signals RD, RG and VOD are transmitted from a control circuit area 318 to the pixels in each row by way of metal conductors (signal lines) 319. In a practical device, there may be more than three signals connected together between pixels, but three signals are shown here to illustrate the principles. The external connections to signals such as RD, RG and VOD may be made with bond wires, solder balls or bumps (as described below with reference to FIG. 3c) or other techniques. As shown in FIG. 3a, the connection between the signals may be predominantly, or exclusively, made in one direction, such as the horizontal direction shown, in order to simplify the interconnections and allow the use of only a single layer of metal. With, for example, a large enough area outside the active area of the sensor, or with two or more layers of metal, interconnections may easily be made in two dimensions, if the extra cost can be justified.

In contrast to the shared signal lines of sensor circuit 310, as indicated at the upper portion of FIG. 3*a*, each analog-to-digital converter 325-11 to 325-44 of signal processing circuit 320 is coupled to processing circuit 328-1 by way of an individual conductor (signal line) 329 in order to maximize data transfer and processing.

Figure 3C:
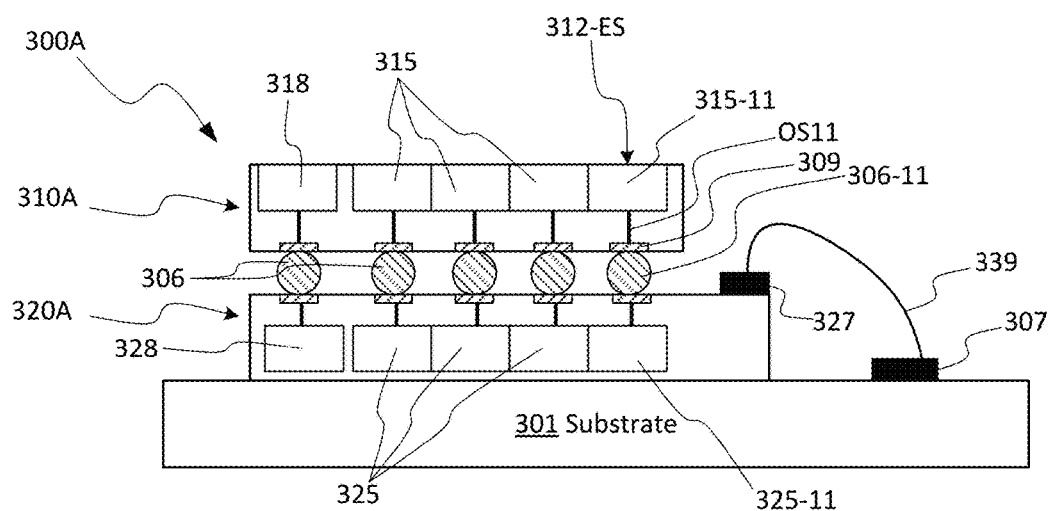

FIG. 3*c* illustrates exemplary electron detector 300A comprising electron sensor 310A, an ASIC (signal processing circuit) 320A and a substrate 301. Substrate 301 provides mechanical support for the electron detector 300A and allows external electrical connections (not shown) to the electron detector 300A. Substrate 301 may comprise silicon or a ceramic material. Electron sensor 310A and ASIC 320A are fabricated on separate silicon substrates (dies or chips) that are then stacked on top of one another, as shown. Alternatively, electron sensor 310A and ASIC 320A may be placed on opposite sides of substrate 301, or side-by-side on the substrate 301 (not shown). Electron sensor 310A is preferably a multi-pixel electron sensor similar to that illustrated in FIGS. 3*a* and 3*b*, and even more preferably includes pixels such as those described below, for example, with reference to FIGS. 4*a* and 4*b*. During operation, electron detector 300A is positioned such that electron sensitive surface 312-ES faces a sample or other electron source, whereby detected electrons are incident on electron sensitive surface 312-ES and are detected as described herein.

Electron sensor 310A is electrically connected to ASIC 320A by solder balls or bumps 306. In a preferred embodiment, the output signal generated by each pixel 315 of electron sensor 310A is transmitted by way of an associated solder ball/bump 306 to an associated analog-to-digital converter 325 of ASIC 320A. For example, output signal OS11 generated by pixel 315-11 is transmitted by way of an associated conductor to a first pad 309 disposed on the lower surface of sensor 310A, and from first pad 309 by way of associated solder ball/bump 306-11 to a second pad disposed on ASIC 320A, from which output signal OS11 is transmitted to the input terminal of associated analog-to-digital converter 325-11. One or more solder balls/bumps 306 may also be used to transmit signals from ASIC 320A (e.g., from circuit 328) to control circuit 318 of sensor 310A. These balls or bumps also provide mechanical support for electron sensor 310A and provide thermal conductivity to electron sensor 310A. Solder balls or bumps may instead be used to directly mount electron sensor 310A to substrate 301 (not shown). Metal pads may also be provided on electron sensor 310A to enable wire bonds to provide electrical connections to electron sensor 310A, for example to surface 312-ES of electron sensor 310A.

ASIC 320A may be mounted directly to substrate 301 as shown, or may be mounted and electrically connected to substrate 301 by solder balls or bumps (not shown). If ASIC 320A includes through-silicon vias, then solder balls or bumps may be used on both sides of ASIC 320A. Metal pads 307 and 327 and/or wire bonds 339 may be used to make electrical connections between ASIC 320A and substrate 301. Similar wire bond connections may be made between sensor 310A and substrate 301, or all connections between substrate 301 and sensor 310A may be made through ASIC 320A. ASIC 320A may comprise a single ASIC or two or more ASICs. For example, in one embodiment, ASIC 320A may comprise two ASICs, one ASIC containing primarily analog functions and the other ASIC containing primarily digital functions. Additional integrated circuits, such as a fiber-optic transmitter or a fiber-optic receiver (not shown) may also be mounted on substrate 301.

ASIC 320A preferably includes analog-to-digital converters 325 configured to digitize output signals from pixels 315 of electron sensor 310A. In one embodiment, ASIC 320A includes one analog-to-digital converter 325 for each pixel 315 so that all pixels 315 can be digitized in parallel at high speed, such as at a speed of 100 MHz or higher. With a high digitization rate, such as 100 MHz or higher, each pixel 315 may detect, at most, a few electrons per clock period, so each analog-to-digital converter 325 may only need 8, 6 or fewer bits. It is easier to design a converter with a smaller number of bits to operate at high speed. An analog-to-digital converter with a small number of bits may occupy a small area of silicon making it practical to have a large number, such as 1024 or more on one ASIC.

ASIC 320A preferably implements part of the method shown in FIG. 2. For example, when the electron detector 320A is used as a back-scattered electron detector, ASIC 320A may implement step 208, or when the electron detector is used as a secondary electron detector, ASIC 320A may implement step 212. ASIC 320A may further incorporate circuits to generate the first pixel clock signal or the second pixel clock signal described in FIG. 2, or may receive a pixel clock signal from an external circuit.

When the electron detector 300A is used as a secondary electron detector, ASIC 320A may implement a de-scanning of secondary electrons similar in result to that implemented by electron optics in the '791 patent cited above. ASIC 320A may sum signals from a group of pixels corresponding to secondary electrons emitted from the sample into one range of angles and output that sum as one signal. As the beam deflection changes, ASIC 320A may sum a different group of pixels under the changed deflection that corresponds to approximately the same range of angles. Since the same master clock is used to generate or synchronize the beam deflection and to generate or synchronize the first and second pixel clocks, the ASIC 320A has the necessary timing information to adjust which groups of pixels are summed together in synchrony with the beam-deflection scan.

When the electron current is low and the pixel clock rate is high enough such that the average number of electrons per pixel is much less than one, then the charge collected in a single pixel in a single period of the pixel clock period can be used to determine whether an electron was detected in that pixel in that clock period, and, if detected, to determine an approximate energy of that electron. The boron coating on the electron sensor surface is necessary to enable this capability. Without a boron coating, few, or no, electrons are created per incident electron when the incident electron energy is less than about 1 keV. With an approximately 5-nm thick boron coating, about 100 electrons are created per incident 1 keV electron. Such a signal can be detected above the noise level if the floating diffusion capacitance is small enough to generate more than about 10 pV per electron. In one embodiment, the floating diffusion capacitance is small enough that the floating diffusion generates more than about 20 pV per electron. For such low level signals, coupling each pixel by as short a path as possible to the corresponding analog to digital converter is important for keeping the noise level low and the stray capacitances low. Attaching the electron sensor directly to the ASIC allows for a very short path from each pixel to the corresponding analog-to-digital converter.

When individual electrons can be detected, ASIC 320A may use the signal level to determine an approximate energy of that electron. ASIC 320A may further threshold, count or bin incident electrons according to their energies in order to detect or classify one or more types of defect or material on the sample.

Figure 4A:
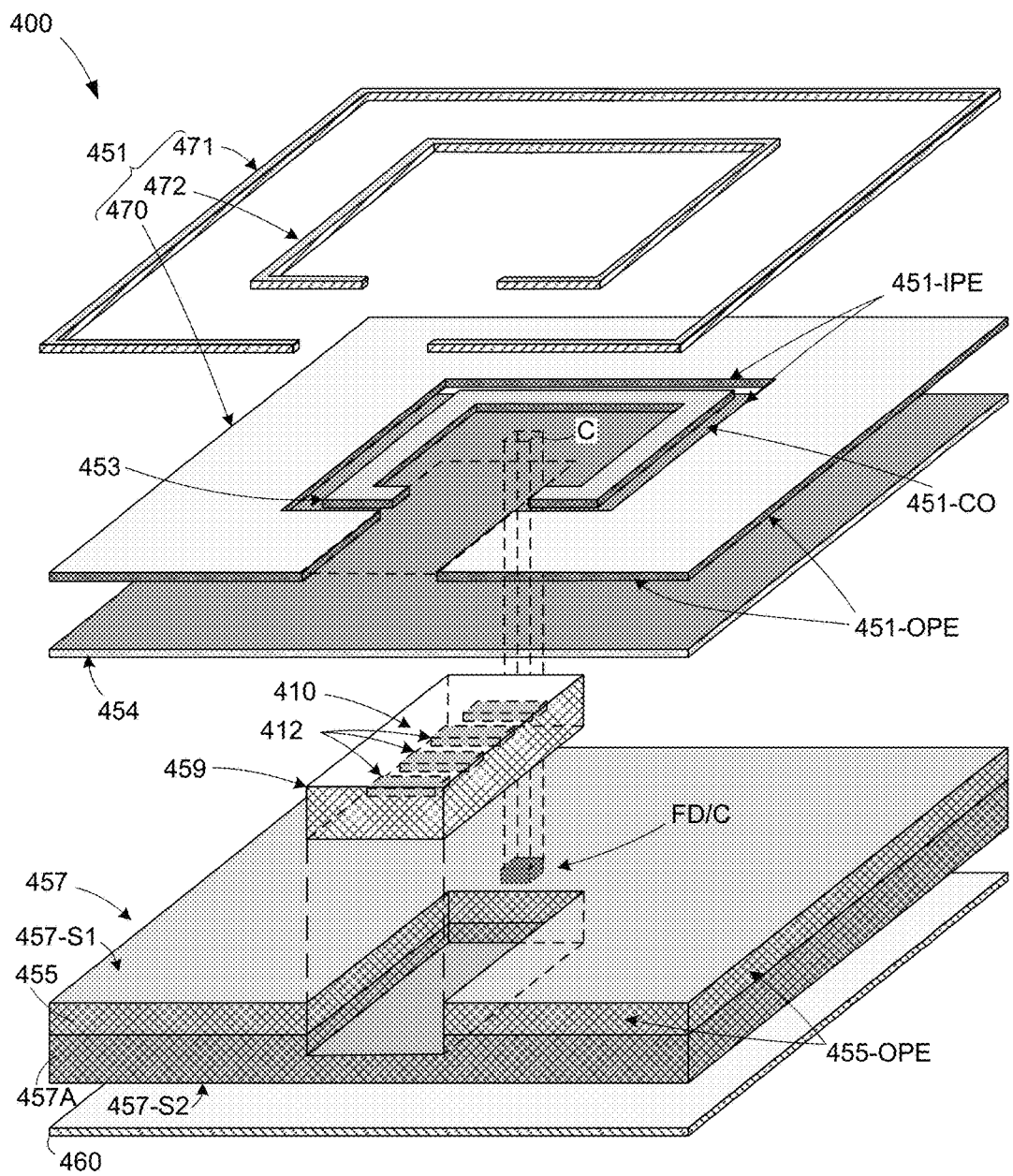
FIGS. 4a and 4b illustrate in exploded and assembled front/top perspective views a single pixel electron sensor according to an exemplary specific embodiment of the present invention.
Figure 4B:
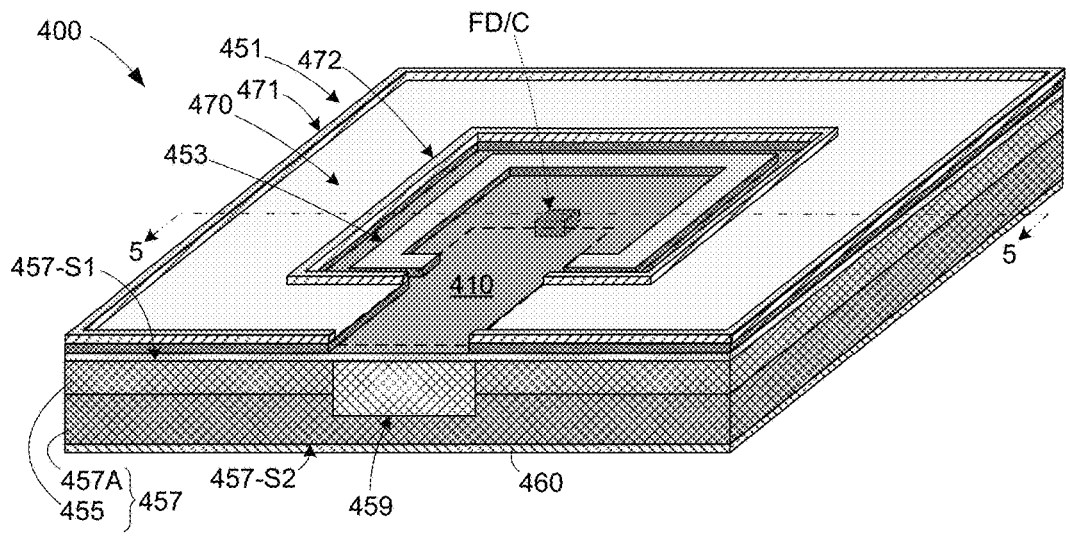

FIGS. 4a and 4b are exploded and assembled perspective views, respectively, showing a simplified pixel 400 of an electron sensor (e.g., sensor 310 described above with reference to FIG. 3a) according to another exemplary specific embodiment of the present invention. Similar to the pixels described above, pixel 400 preferably has a size (nominal lateral dimension) of between approximately 200 µm and 250 µm.

Referring to FIG. 4a, similar to the pixel features mentioned above, pixel 400 includes a p-type electron-sensitive layer 457A, an n-type buried channel layer 455 disposed over the p-type electron-sensitive layer 457A, an n+ floating diffusion FD formed in n-type buried channel layer 455, an amplifier 410, and an optional pure boron layer 460 disposed below the p-type electron-sensitive layer 457A.

Buried channel layer 455 and electron-sensitive layer 457A are disposed in an epitaxial silicon layer 457 such that an upper extent of buried channel layer 455 coincides with (forms) a top (first) surface 457-S1 of epitaxial silicon layer 457, and electron-sensitive layer 457A comprises a portion of epitaxial silicon layer 457 disposed between buried channel layer 455 and a bottom (electron-sensitive) surface 457-S2 of epitaxial silicon layer 457. Epitaxial silicon layer 457 has a thickness preferably between about 10 µm and 100 µm, and is lightly p-doped such that the resistivity is, in one embodiment, between about 10 and 2000 Ωcm. A thicker epi layer provides more mechanical strength, but may generate more dark current. A lower doping level (higher resistivity) may be required for a layer thicker than about 20 µm or 30 µm in order to maintain a fully depleted state in the bulk of the silicon. Too low a doping level is not preferred as that will lead to a higher dark current.

Buried channel layer 455 is created under top surface 457-S1 of epitaxial silicon layer 457 by n-type doping diffused using known techniques. The doping concentration of buried channel layer 455 must be orders of magnitude greater than the doping concentration in epitaxial silicon layer 457, so that epitaxial silicon layer 457 is fully depleted during operation. In one preferred embodiment, the concentration of n-type dopants in the buried channel layer 455 is between about $10^{16}$ and $5 \times 10^{16}$ cm$^{-3}$.

Floating diffusion FD comprises a relatively small n+ doped region disposed in buried channel layer 455 that is configured to collect electrons generated in pixel 400 in response to incident back-scattered or secondary electrons. In one preferred embodiment, floating diffusion FD has a nominal lateral size between about 1 and 5 µm, and the concentration of n-type dopants in floating diffusion FD is between about $10^{19}$ and $10^{21}$ cm$^{-3}$. A connection for transmitting stored charges to amplifier 410 is made to floating diffusion FD using known techniques.

Pure boron layer 460 is preferably deposited on the back or bottom surface 457-S2 of epitaxial silicon layer 457. Boron layer 460 is preferably between about 2 nm and 10 nm thick, such as a thickness of about 5 nm. As explained in U.S. patent application Ser. No. 13/792,166 (cited above), during the boron deposition process, some boron diffuses a few nm into the epitaxial silicon layer 457 to form a thin, very highly doped p+ layer adjacent to the pure boron layer 460. This p+ layer is important for optimal operation of the sensor. This p+ layer creates an electric field that drives electrons towards the buried channel 455, reduces dark current from the back surface of the epitaxial silicon layer 457, and increases the conductivity of the silicon surface allowing the sensor to function at high incident electron currents as well as low currents. In one embodiment, during deposition of the pure boron layer 460, additional boron is allowed to diffuse into the silicon. This can be done by one of several methods. In one exemplary method, a thicker layer of boron is deposited than the final desired thickness (for example a 6 nm to 8 nm layer may be deposited when a 5 nm final thickness is required) and then the boron is allowed to diffuse into silicon epitaxial layer 457 by keeping the sensor at the deposition temperature or a higher temperature (such as between about 800° C. and 950° C.) for a few minutes. In another exemplary embodiment, a few nm thick layer of boron may be deposited on the silicon, then the boron may be driven in at the deposition temperature or a higher temperature, and then the final desired thickness of boron (such as 5 nm) may be deposited.

According to an aspect of the present embodiment, amplifier 410 is formed in and over an elongated p-well region 459 that extends vertically from top surface 457-S1 into electron-sensitive layer 457A, and extends outward from a point adjacent to the pixel's central region C (i.e., toward peripheral outer edge 455-OPE of n-type buried channel layer 455). Note that p-well region 459 is shown separated from silicon epitaxial layer 457 in FIG. 4a for descriptive purposes, but in fact comprises a p-type doped region of silicon epitaxial layer 457. In alternative embodiments, p-well 459 is either entirely contained within the square-shaped peripheral boundary of pixel 400, or extends past the peripheral boundary (e.g., into an adjacent pixel). In one embodiment, p-well 459 is formed by implanting boron with a concentration substantially higher than the dopant concentration in silicon epitaxial layer 457, and then n-type channel regions 412 of the various transistors of amplifier 410 are formed in p-well 459, whereby p-well 459 serves to prevent electrons from migrating directly from the epitaxial silicon layer into channel regions 412. In one embodiment, the p-well extends under the floating diffusion and the channel region of the pixel's reset transistor (discussed below with reference to FIG. 7) to prevent electrons from migrating directly from the epitaxial silicon layer into the floating diffusion.

As indicated in FIG. 4a, one or more dielectric layers 454 overlay the buried channel. Dielectric layers 454 may comprise a single silicon dioxide layer or a silicon nitride layer on top of a silicon dioxide layer or a silicon oxide layer on top of a silicon nitride layer on top of a silicon dioxide layer. Individual layer thicknesses may be between about 20 nm and 50 nm.

According to another aspect, pixel 400 further includes a resistive gate 451 comprising one or more polycrystalline or amorphous silicon gate structures 470 disposed on dielectric layer(s) 454 and configured to cover most of upper surface 457-S1. As indicated in FIG. 4a, resistive gate 451 includes an outer peripheral edge 451-OPE that substantially aligns with the periphery of pixel 400 (i.e., generally aligns with outer peripheral edge 455-OPE of buried channel layer 455), and defines a central opening 451-CO such that an inner peripheral edge 451-IPE of resistive gate 451 (i.e., the inner edge of gate structure 470) substantially surrounds and is spaced laterally from central pixel region C (e.g., as indicated in FIG. 4b). In one embodiment gate structure 470 comprises polycrystalline silicon having a relatively light doping level (e.g., having a resistivity greater than about 30Ω per cm) such that, when a decreasing potential difference is applied between inner peripheral edge 451-IPE and outer peripheral edge 451-OPE, resistive gate 451 generates an associated electric field that biases electrons in buried channel layer 455 toward the pixel's central region C in the manner described below with reference to FIGS. 5a and 5b. To facilitate operating resistive gate 451 such that electrons from all peripheral lateral areas of pixel 400 are biased toward central region C for collection by floating diffusion FD, resistive gate 451 also includes elongated conductors (e.g., metal wires) 471 and 472 disposed on gate structure 470 along and adjacent to outer peripheral edge 451-OPE and inner peripheral edge 451-IPE, respectively. As described below, a negative potential relative to elongated conductor 472 is applied to elongated conductor 471, such as a voltage of −5 V. The resulting potential difference between conductors 471 and 472 generates a decreasing potential in a substantially radial direction in gate structure 470 (i.e., between inner peripheral edge 451-IPE and outer peripheral edge 451-OPE) that drives electrons in the buried channel (see FIG. 4b) towards the floating diffusion FD. Additional connections to gate structure 470 may be provided between conductors 471 and 472 and held at potentials intermediate to those applied to conductors 471 and 472 so as to modify the potential gradient in resistive gate 451. Additional detail regarding the composition of resistive gate 451 can be found in U.S. patent application Ser. No. 11/805,907 entitled "Inspection System Using BackSide Illuminated Linear Sensor" and filed by Armstrong et al. on May 25, 2007. This patent application is incorporated by reference herein in its entirety.

According to another aspect, pixel 400 further includes one or more optional additional gate structures disposed between resistive gate 451 and floating diffusion FD to further drive electrons onto floating diffusion FD, or to control when the electrons are collected/accumulated on floating diffusion FD. For example, pixel 400 includes a C-shaped highly-doped polycrystalline gate structure 453 disposed on dielectric layers 454 and inside inner peripheral edge 451-IPE of resistive gate 451. Constant or switched voltages may be applied to gate structure 453 to control and ensure efficient charge transfer from the portions of buried channel layer 455 under resistive gate 451 to floating diffusion FD. In one embodiment described below with reference to FIGS. 5a and 5b, gate structure 453 is utilized as a summing gate to which a low voltage, such as 0V (relative to bottom surface 457-S2 or boron layer 460), is applied during reset, and a high voltage, such as 10V, is applied during readout. In addition to summing gate 453, one or more additional gates, such as a buffer gate, a transfer gate, and an output gate may be formed by associated additional gate structures placed between resistive gate 451 and floating diffusion FD. Such gates are well known in CCD technology and may be operated in a similar manner in this electron sensor. See, for example, J. R. Janesick, "Scientific Charge-Coupled Devices", SPIE Press, 2001, pp 156-165.

FIG. 4b shows simplified pixel 400 in a partially assembled state. As indicated, most of pixel 400 (i.e., most of top surface 457-S1) is covered by amorphous silicon or poly-silicon gate structure 470, which forms resistive gate 451. The exposed region (indicated by dashed-line box) above p-well region 459 is indicated for illustrative purposes as being empty, but in fact includes various connection structures and gates associated with the transistors forming amplifier 410 and a reset transistor RT. An exemplary layout of these structures and gates is provided below with reference to FIG. 7. In one embodiment (not shown), summing gate 453 overlaps (i.e., extends over and is separated by a suitable insulator to keep them electrically isolated) inner peripheral edge 451-IPE of resistive gate 451. This overlapped arrangement prevents fringe electric fields in the silicon under the gap between the two gate structures. These fringe fields can trap electrons in the buried channel or cause them to move in unexpected directions.

Figure 5A:
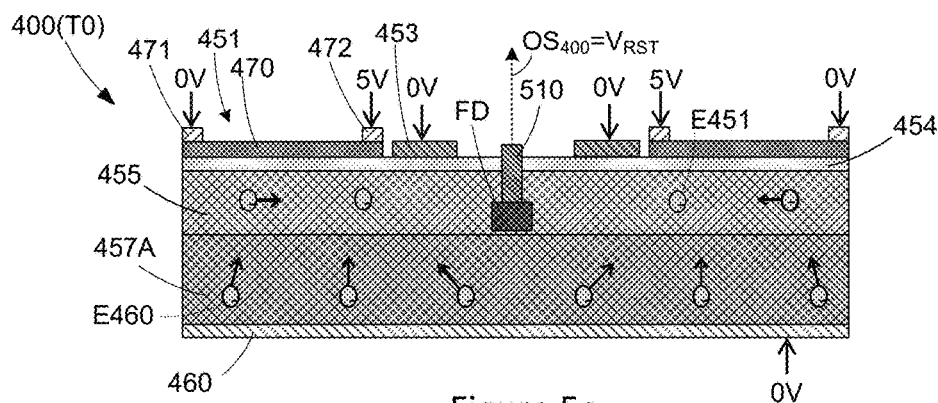
FIGS. 5a and 5b are simplified cross-sectional views showing the pixel of FIG. 4b during operation.
Figure 5B:
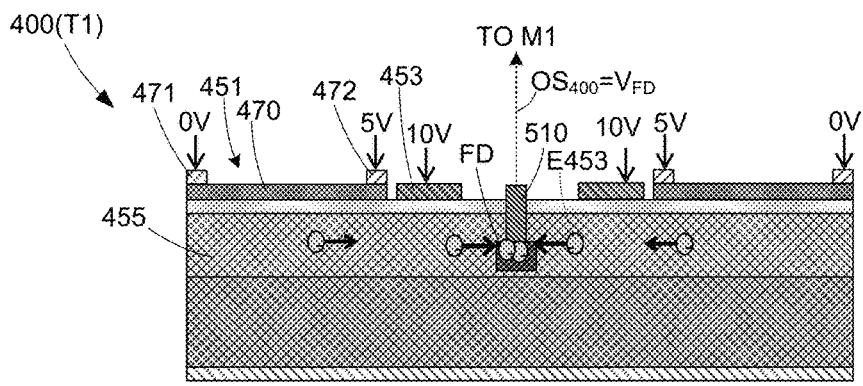

FIGS. 5a and 5b are simplified cross-sectional views showing pixel 400 during an exemplary detection/readout cycle (operation), where FIG. 5a depicts pixel 400 at a time T0 during or immediately after floating diffusion is reset to a reset voltage (i.e., $OS_{400}$ is equal to a reset voltage level $V_{RST}$), and FIG. 5b depicts pixel 400 at a subsequent time T1 when output signal $OS_{400}$ is read out in the manner described above (i.e., when $OS_{400}$ is equal to a voltage level $V_{FD}$ determined by the number of electrons accumulated on floating diffusion FD between times T0 and T1). Note that the individual layers shown in FIGS. 5a and 5b are not drawn to scale, but are exaggerated in order to show them more clearly.

Referring to FIG. 5a, the back surface coated by pure boron layer 460 is preferably held at a similar potential to the outer edge of the resistive gate (such as 0 V in the example). Since boron is conductive and since the silicon immediately under pure boron layer 460 is highly doped with boron, the back surface may be sufficiently conductive that connecting to it at one, or a few, locations provides a sufficiently low impedance path for operation of the sensor at high incident currents, such as a current of about 10 to 50 nA. The electric fields formed by these potential differences drive electrons (such as E460) created in the epitaxial silicon (electron sensitive) region 457A by back-scattered or secondary electrons incident on the sensor through pure boron layer 460 towards buried channel 455 as illustrated by the arrows on the electrons. A potential difference is applied to resistive gate 451 between the outer edge of pixel 400 and the inner edge of gate structure 470 by way of conductors 471 and 472. In one example, 0V is applied to the outer edge by way of conductor 471, and 5V is applied to the inner edge by way of conductor 472, as shown. The resulting potential difference in gate structure 470 produces an electric field that drives electrons (such as E451) disposed in buried channel 455 toward the center of pixel 400 (i.e., causes these electrons to move toward floating diffusion FD).

In the example depicted in FIGS. 5a and 5b, summing gate 453 is used to control and drive the electrons into floating diffusion FD. For example, as indicated in FIG. 5a, when transfer of electrons to floating diffusion FD is to be blocked (e.g., during reset), the voltage applied to summing gate is significantly lower than that applied to conductor 472, whereby the electric field prevents electrons from readily flowing to floating diffusion FD and causes them to accumulate in buried channel 455 underneath 472 (as indicated by electron E451). Conversely, as indicated in FIG. 5b, when electrons are to be transferred to floating diffusion FD (e.g., right before readout), summing gate 453 receives a relatively high positive potential (relative to the voltage applied to conductor 472, e.g., 10V relative to 5V applied to conductor 472, as shown), causing electrons, such as E453, underneath conductor 472 to move toward floating diffusion FD. Since floating diffusion FD acts as a capacitor, the voltage $V_{FD}$ on the floating diffusion FD at readout becomes more negative as more charge (electrons) accumulates. For small signals, the change in voltage $V_{FD}$ is proportional to the accumulated charge (i.e. the capacitance of the floating diffusion FD is substantially constant), but as the amount of charge increases, the capacitance changes and the voltage increase is no longer linear. Although operation in the linear regime is usually preferred, in one embodiment, operation in a non-linear regime may be used to compress a high dynamic range signal. Since the sensitivity (charge-to-voltage conversion ratio) and speed depend on the capacitance of floating diffusion FD being small, it is generally preferable to keep floating diffusion FD as small as practical and minimize the size (and hence capacitance) of the structures connected to floating diffusion FD, including the channel of the reset transistor and the connection to the gate of transistor M1.

Note that the voltage values cited in the example above are merely examples. Different values may be used, and optimal values depend on many factors including the desired speed of operation of the sensor, the geometries of the one or more gates, the doping profiles and the thicknesses of the dielectric layer(s) 454. Note also that it is typically convenient to define the backside (i.e., electron sensitive side) of a sensor as 0V (note that this voltage may be far from ground potential if the electron detector is floated at some potential other than ground), and conductor 471 will preferably be connected to a similar potential.

In an alternative embodiment, instead of switching the reset transistor and the voltages on the various gates of each pixel, the reset transistor and the various gates are held at fixed potentials so that electrons generated in the epitaxial silicon (electron sensitive) region 457A can flow continuously to the floating diffusion FD. In this mode, the voltage on the reset gate RG (FIG. 3b) must be held at a voltage that causes the reset transistor RT to be in a high resistance, partially conductive, state (such as a channel resistance between about 500 kΩ and a few MΩ) rather than "off" (which corresponds to a channel resistance of hundreds of MΩ or higher) or "on" (which corresponds to a channel resistance of a few kΩ or lower).

In this embodiment, the gate or gates between the inner peripheral edge of resistive gate 451 and the floating diffusion FD must each be held at successively higher voltages, all higher than that of conductor 472, so that electrons in the buried channel 455 will be driven towards floating diffusion FD. For example, if conductor 472 is at a potential of 5V, then summing gate 453 could be held at a voltage of 6V. If there were another gate (not shown) between the inner peripheral edge of resistive gate 451 and the summing gate 453, then that other gate could, for example, be held at 6V and the summing gate 453 at 7V. The reset drain RD must be held at a voltage significantly more positive than the inner-most gate (such as summing gate 453) so as to keep the floating diffusion FD at a sufficiently high potential relative to all the gates to attract the electrons in the buried channel. For example the reset drain RD might be held at 15V.

As will be readily understood, the channel of the reset transistor RT and the capacitance of the floating diffusion FD form an RC time constant that determines how quickly a voltage on the floating diffusion FD decays back to the reset drain RD voltage after electrons arrive at floating diffusion FD. For example, if the analog-to-digital converters are sampling each pixel at 100 MHz (i.e. once every 10 ns), then an RC time constant of approximately 20 ns or 30 ns might be appropriate. In this example, if the capacitance of the floating diffusion is about 10 fF, then the reset gate RG voltage should be set so that the resistance of the channel of the reset transistor RT is about 2.5MΩ so as to give a time constant of about 25 ns.

This embodiment is made possible by the sensor disclosed herein because each pixel is connected to its own analog to digital converter. In a conventional two-dimensional CCD or CMOS image sensor, charges need to be stored and read out serially as the number of analog to digital converters is fewer than the number of pixels. Furthermore conventional CMOS image sensors use transistors and gates with surface channels rather than buried channels. Surface channels, in contrast to buried channels, generate noise and cannot transfer small charges without loss.

Figure 6:
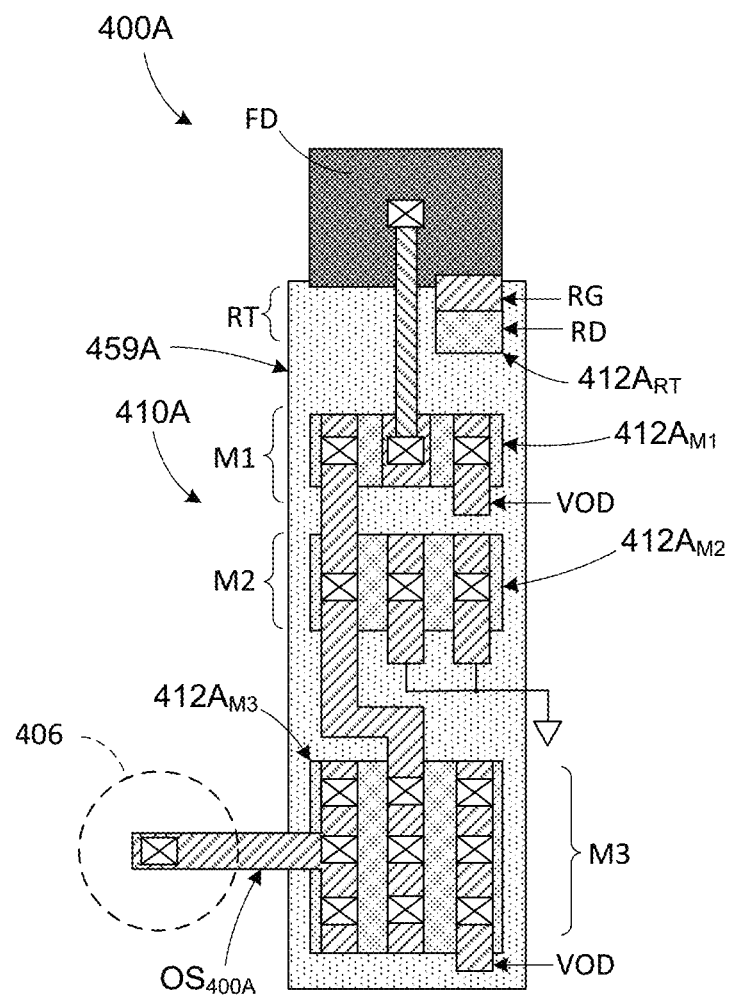
FIG. 6 is a simplified plan view showing an exemplary layout for an amplifier utilized by a pixel according to an alternative embodiment of the present invention.

FIG. 6 is a simplified plan view showing a partial pixel 400A, and in particular shows an exemplary layout including a floating diffusion FD, an amplifier 410A and a reset transistor RT utilized by pixel 400A according to an exemplary specific embodiment of the present invention. In one embodiment, pixel 400A is substantially identical to pixel 400 described above (i.e., where floating diffusion FD is located in a central region of pixel 400A), so the non-illustrated portions of pixel 400A are omitted for brevity. In FIG. 6, doped regions (e.g., floating diffusion FD) are indicated by dot-type shaded regions, conductive structures (e.g., polysilicon or metal) are indicated by slanted-line regions, and vertical metal vias are indicated by boxes including "X" symbols. Note that the various amplifier polysilicon or metal structures are separated (i.e., not contiguous), and are patterned and interconnected using standard techniques. In this example, reset transistor RT is disposed directly below floating diffusion FD, and amplifier 410A includes transistors M1, M2 and M3 that are connected and function in a manner similar to that described above with reference to FIG. 3b. Additional connections and vias associated with the structures shown in FIG. 6 are omitted for clarity.

Referring to the upper portion of FIG. 6, floating diffusion FD is disposed adjacent to p-well region 459A, which is formed in the manner described above and includes various n-type channel regions associated with reset transistor RT and transistors M1 to M3 of amplifier 410A. For example, reset transistor RT includes an N-type channel region $412A_{RT}$ that is disposed in p-well region 459A immediately below and connected to floating diffusion FD and receives reset voltage RD, and includes a gate structure that is controlled by reset gate signal RG. Transistor M1 includes an N-type channel region $412A_{M1}$ that is disposed in p-well region 459A immediately below reset transistor RT and includes a gate structure connected to floating diffusion FD, a drain structure connected to system voltage VOD, and a source structure connected to a drain structure of transistor M2 and a gate structure of transistor M3. Transistor M2 includes an N-type channel region $412A_{M2}$ that is disposed in p-well region 459A immediately below transistor M1 and includes gate structure and source structures connected to ground. Transistor M3 includes an N-type channel region $412A_{M3}$ that is disposed in p-well region 459A immediately below transistor M2 and includes a drain structure connected to system voltage VOD, and a source structure that serves to transmit an output signal $OS_{400A}$ of pixel 400A to an associated analog-to-digital converter by way of a metal pad or solder ball/bump 406 in an arrangement similar to that shown and described with reference to FIG. 3c. Note that the metal pad for OS may lie at a location away from the center of pixel 400A, and, in one embodiment, may overlay part of one, or more, adjacent pixels.

In one embodiment, reset transistor RT is controlled to discharge floating diffusion FD to reset voltage RD using a reset gate voltage RG that is sufficiently positive to turn on reset transistor RT. RD should be more positive than the voltages applied to the various pixel gates (e.g., resistive gate 451 and summing gate 453, described above with reference to FIGS. 4a and 4b). For example, referring to the example shown in FIG. 5b in which summing gate 453 is controlled using 10V, reset drain voltage RD might have a voltage value between about 15V and 20V. It is necessary to periodically turn on reset transistor RT to discharge the electrons that have accumulated in floating diffusion FD. When the incident electron current hitting the pixel is small, it may not be necessary to discharge (reset) the floating diffusion every time that the pixel is read out. When the incident current is high, floating diffusion FD may need to be reset every pixel clock period.

Figure 7:
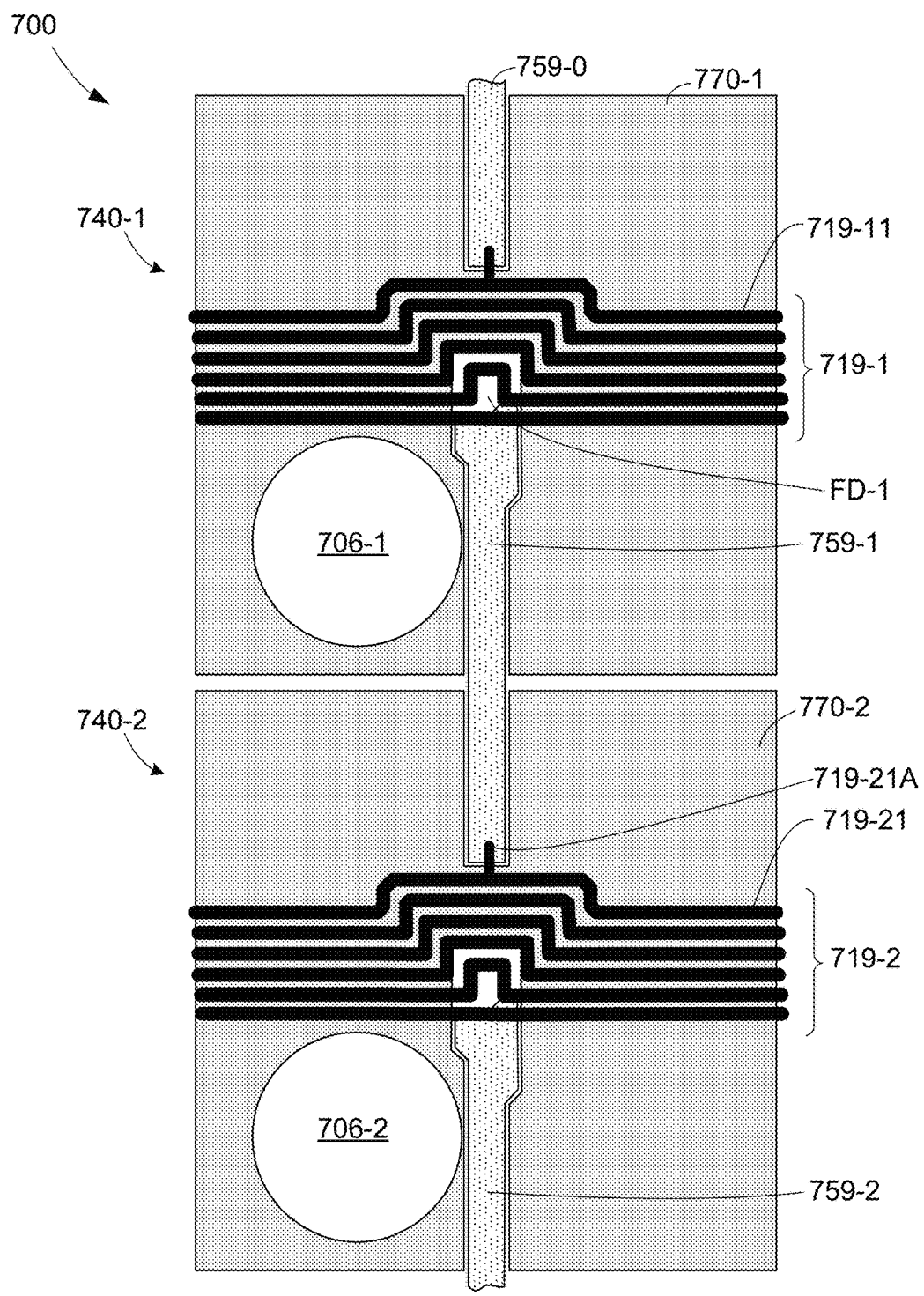
FIG. 7 is a simplified plan view showing a pixel layout according to another alternative embodiment of the present invention.

FIG. 7 shows a partial simplified exemplary sensor 700 that is arranged in accordance with another embodiment of the present invention, and illustrates an alternative layout pattern in which the p-well region 759-1 of pixel 740-1 extends into the space otherwise occupied by an adjacent pixel 740-2, and at least one control signal utilized by pixel 740-1 is connected to a signal line 719-21 passing over adjacent pixel 740-2. The p-well regions and signal lines discussed in this example are formed and function in a manner similar to p-well region 459 and signal lines 319 discussed in additional detail above with reference to FIGS. 4a and 3a, respectively. Note that metal line bundles 719-1 and 719-2 extend over all other structures, are separated from underlying polysilicon structures (e.g., resistive gate 770-1) by a borophosphosilicate glass layer or other dielectric material, and are connected by way of metal vias (not shown) to the underlying structures. Note also that several structures of pixels 740-1 and 740-2 that are described above are omitted in FIG. 7 for clarity and brevity.

As mentioned above, the amorphous or polycrystalline gate structure utilized to generate the resistive gate (and any additional gates such as summing gate 453, discussed above) in each pixel essentially entirely covers the pixel area except for the central region (i.e., to allow for access to the floating diffusion) and the area in which a p-well is formed. In the example described above with reference to FIGS. 4a and 4b, p-well region 459 is entirely disposed within the square-shaped boundary of each pixel, so the resistive and summing gates extend entirely around the remaining perimeter of pixel 400. However, in some cases the M3 amplifier transistor requires a width that causes it to extend beyond the lower pixel boundary.

To accommodate the extended M3 transistor shape, the pixels of sensor 700 are configured to share a portion of their space with an adjacent pixel. Specifically, to provide space for both its own elongated p-well region 759-1 and the portion of p-well region 759-0 extending downward from the pixel above (not shown), resistive gate structure 770-1 of pixel 740-1 is formed in a generally "H" shaped pattern. Similarly, resistive gate structure 770-2 of pixel 740-2 is formed in the same "H" shaped pattern to accommodate the lower portion of p-well 759-1 and the upper portion of p-well region 759-1.

As also discussed above, pixels in each row of sensor 700 share common signal lines that extend along the entire row to a peripherally positioned control circuit (not shown). In the case shown in FIG. 7, signal line bundle 719-1 extends over the row including pixel 740-1, and signal line bundle 719-2 extends over the row including pixel 740-2. Due to the extension of the p-well regions into adjacent pixels, in some cases it becomes efficient to provide signal connections from the signal line bundle extending over an adjacent pixel. For example, signal line 719-21 is connected by way of conductor 719-21A to a transistor structure (not shown) disposed in p-well region 759-1, whereby a signal (e.g., 0V/ground) is provided to pixel 740-1 from signal line bundle 719-2 passing over adjacent pixel 740-2. Similarly, signal line 719-11 of signal line bundle 719-1 provides a signal to a transistor structure (not shown) disposed in p-well region 759-0.

FIG. 7 also depicts a preferred position of solder bumps/balls 706-1 and 706-2 in pixels 740-1 and 740-2 (i.e., in the lower left quarter of each pixel area). Note that the depicted sizes of solder bumps/balls 706-1 and 706-2 in pixels 740-1 and 740-2 are generally accurate for a 250 μm nominal lateral (e.g., diagonal) pixel size and a standard solder bump/ball. In alternative embodiments with different sized pixels or different sized solder balls or bumps, the relative sizes of the pad and the pixel could differ significantly from those illustrated in FIG. 7.

In an embodiment, the electron detectors described herein may also detect X-rays. If an X-ray emitted by the sample has enough energy, such as an energy of about 1 keV or higher, it may generate enough electrons when absorbed in the electron sensor to be detected.

The systems and methods described herein may be used with any of the systems and methods described in U.S. Published Patent Application 2014/0151552, entitled "Tilt-Imaging Scanning Electron Microscope" and filed by Jiang et al. on Mar. 18, 2013, U.S. Published Patent Application 2013/0341504, entitled "Auger Elemental Identification Algorithm", and filed by Neill et al. on Jun. 7, 2013, U.S. Published Patent Application 2011/0168886, entitled "Charged-particle energy analyzer" and filed by Shadman et al. on Mar. 17, 2011, and U.S. Published Patent Application 2010/0208979, entitled "Use of design information and defect image information in defect classification" and filed by Abbott et al. on Feb. 16, 2009. All these applications are incorporated by reference herein.

The various embodiments of the structures and methods of this invention that are described above are illustrative only of the principles of this invention and are not intended to limit the scope of the invention to the particular embodiments described. For example, the size, shape and layout of the structures within a pixel may differ significantly from those shown herein. The amplifier in a single pixel may comprise one, two or three stages for example. More, or fewer, gates may be used to control the transfer of charge to the floating diffusion. The ASIC within the electron detector may further comprise an FPGA or a digital signal processor to implement algorithms for processing or analyzing the signals from the detector. The ASIC may also include serial transmitter circuits and/or serial receiver circuits to send data to an image processing computer and/or receive commands.

Therefore, the scanning electron microscopes, sensors and methods described herein are not intended to be limited to the particular embodiments shown and described, but are to be accorded the widest scope consistent with the principles and novel features herein disclosed.

The invention claimed is:
1. A method of inspecting a sample comprising:
generating a master clock signal;
generating a beam-deflection scan synchronized with the master clock signal;
generating a first pixel clock signal synchronized with the master clock signal;
generating a primary electron beam and focusing the primary electron beam on a sample;
using the beam-deflection scan to scan the primary electron beam over an area of the sample;
collecting back-scattered electrons from the sample in a first multi-pixel solid state detector;

generating first digitized signals by digitizing a first output signal generated by each pixel of the first multi-pixel solid state detector in each period of the first pixel clock signal; and using the first digitized signals to determine the presence or absence of a defect in the area of the sample, wherein collecting back-scattered electrons comprises causing the back-scattered electrons to pass through a pure boron layer on an electron-sensitive surface of said first multi-pixel solid state detector, and wherein each said pixel of said first multi-pixel solid state detector comprises a p-type electron-sensitive layer, an n-type buried channel layer disposed on the electron-sensitive layer, an n+ floating diffusion disposed in the buried channel layer, and an amplifier coupled to the floating diffusion.

2. The method of claim 1, further comprising:
generating a second pixel clock signal synchronized with the master clock signal;
collecting secondary electrons from the sample in a second multi-pixel solid state detector;
generating second digitized signals by digitizing a second output signal generated by each pixel of the second multi-pixel solid state detector in each period of the second pixel clock signal; and
using the first digitized signals and the second digitized signals to determine the presence or absence of a defect in the area of the sample.

3. The method of claim 2, wherein collecting secondary electrons comprises causing the secondary electrons to pass through a second pure boron layer formed on an electron-sensitive surface of the second multi-pixel solid state detector.

4. The method of claim 3, wherein the first pixel clock signal and the second pixel clock signal are generated with the same frequency.

5. The method of claim 1, further comprising determining an approximate energy of a backscattered electron from the first digitized signals.

6. The method of claim 5, further comprising determining a type or a material of the defect in the area of the sample.

7. The method of claim 1, wherein generating and focusing the primary electron beam comprises directing the primary electron beam onto one of an unpatterned semiconductor wafer, a patterned semiconductor wafer, a reticle and a photomask.

8. A method of inspecting a sample comprising:
generating a primary electron beam and focusing the primary electron beam on a sample;
collecting back-scattered electrons from the sample in a first multi-pixel solid state detector;
generating first digitized signals by digitizing an output signal generated by each pixel of the first multi-pixel solid state detector; and using the first digitized signals to determine the presence or absence of a defect in the area of the sample, wherein each said pixel of said first multi-pixel solid state detector comprises:
a p-type electron-sensitive layer configured to generate multiple electrons in response to each said incident electron that enters said electron-sensitive layer through a first surface of said electron-sensitive layer;
an n-type buried channel layer disposed on a second surface of the electron-sensitive layer and configured to collect at least some of the multiple electrons generated by the electron-sensitive layer;
an n+ floating diffusion disposed in the buried channel layer and configured to accumulate at least some of the electrons collected by the buried channel layer such that a voltage of the floating diffusion changes in proportion to a number of said electrons accumulated on the floating diffusion; and
an amplifier configured to generate said output signal in accordance with the voltage of the floating diffusion.

9. The method of claim 8, wherein collecting back-scattered electrons comprises causing the back-scattered electrons to pass through a pure boron layer on an electron-sensitive surface of said first multi-pixel solid state detector.

10. The method of claim 8, further comprising:
collecting secondary electrons from the sample using a second multi-pixel solid state detector;
generating second digitized signals by digitizing a second output signal generated by each pixel of the second multi-pixel solid state detector; and
using the first digitized signals and the second digitized signals to determine the presence or absence of a defect in the sample.

11. The method of claim 10, wherein collecting secondary electrons comprises causing the secondary electrons to pass through a second pure boron layer formed on an electron-sensitive surface of the second multi-pixel solid state detector.

12. The method of claim 8, further comprising determining an approximate energy of a backscattered electron from the first digitized signals.

13. The method of claim 12, further comprising determining a type or a material of the defect in the sample.

14. The method of claim 8, wherein generating said first digitized signals comprises utilizing a plurality of analog-to-digital converters, wherein each of the multiple analog-to-digital converters is operably coupled to receive an associated said output signal generated by an associated pixel of said first multi-pixel solid state detector.

* * * * *